US007468178B2

(12) United States Patent
Tononi et al.

(10) Patent No.: US 7,468,178 B2
(45) Date of Patent: *Dec. 23, 2008

(54) METHODS FOR IDENTIFYING COMPOUNDS THAT MODULATE VIGILANCE STATES

(75) Inventors: Giulio Tononi, San Diego, CA (US);
Chiara Cirelli, San Diego, CA (US);
Paul J. Shaw, San Diego, CA (US);
Ralph J. Greenspan, Coronado, CA (US)

(73) Assignee: Neurosciences Research Foundation, Inc., San Diego, CA (US)

( * ) Notice: Subject to any disclaimer, the term of this patent is extended or adjusted under 35 U.S.C. 154(b) by 221 days.

This patent is subject to a terminal disclaimer.

(21) Appl. No.: 10/830,909

(22) Filed: Apr. 22, 2004

(65) Prior Publication Data

US 2004/0197266 A1      Oct. 7, 2004

Related U.S. Application Data

(63) Continuation of application No. 09/718,828, filed on Nov. 22, 2000, now Pat. No. 6,730,287.

(60) Provisional application No. 60/367,372, filed on Nov. 24, 1999.

(51) Int. Cl.
*A61K 49/00*    (2006.01)

(52) U.S. Cl. .................. 424/9.2; 424/1.11; 424/9.1

(58) Field of Classification Search .............. 424/1.11, 424/1.65, 9.1, 9.2
See application file for complete search history.

(56) References Cited

U.S. PATENT DOCUMENTS

| 5,885,831 | A | 3/1999 | Young et al. |
| 5,968,817 | A | 10/1999 | Sutcliffe et al. |
| 6,436,628 | B1 | 8/2002 | Young et al. |
| 6,730,287 | B1 * | 5/2004 | Tononi et al. ............. 424/9.2 |

FOREIGN PATENT DOCUMENTS

| EP | 0 890 578 | 1/1999 |
| JP | 10502336 | 3/1998 |
| JP | 09804125 | 3/1999 |
| WO | WO 99/24610 | 5/1999 |
| WO | WO 99/57137 | 11/1999 |

OTHER PUBLICATIONS

Anderson, "Human Gene Therapy," *Nature* 392:25-30 (1998).
Andretic et al., "Requirement of circadian genes for cocaine sensitization in drosphilia," *Science* 285:1066-1068 (1999).
Aronstein et al., "Distribution of two GABA receptor-like subunits in the Drosophila CNS," *Invert. Neurosci.* 2:115-120 (1996).
Aston-Jones et al., "Activity of Norepinephrine-Containing Locus Coeruleus Neurons in Behaving Rates Anticipates Fluctuations in The Sleep-Waking Cycle," *Journal of Neuroscience* 1(8):876-886 (1981).

Author Unknown, "The promise of strung-out flies," *Science News* 153:104 (1998).
Bellen, "The Fruit Fly: A Model Organism to Study the Genetics of Alcohol Abuse and Addiction?," *Cell* 93:909-912 (1988).
Belvin et al., "The *Drosophila* dCREB2 Gene Affects the Circadian Clock," *Neuron* 22:777-797 (1999).
Bennett et al., "Improved food medium," *Dros. Inform. Serv.* 46:160 (1971).
Bliwise, *Principles and Practice of Sleep Medicine*, Kryger et al. Eds. (Saunders, Philadelphia, 2nd ed., Chapter 3) (1994).
Boynton et al., "Latheo a new gene involved in associative learning and memory in drosophila-,elongaster identified from P element mutagenesis," *Genetics* 131:655-672 (1992).
Boynton et al., "*latheo*, a New Gene Involoved in Associative Learning and Memory in *Drosophila melanogaster*, Identified from *P* Element Mutagenesis," *Genetics* 131:655-672 (1992).
Brodbeck et al., "Molecular and Biochemical Characterization of the *aaNAT1 (Dat)* Locus in *Drosophila melanogaster*: Differential Expression of Two Gene Products," *DNA and Cell Biology* 17:621-633 (1998).
Chemelli et al., "Narcolepsy in orexin knockout mice: molecular genetics of sleep regulation," *Cell* 98:437-451 (1999).
Chemelli et al., "Narcolepsy in *orexin* Knockout Mice: Molecular Genetics of Sleep Regulation," *Cell* 98:437-451 (1999). (Duplicate of Reference #21).
Cirelli et al., "Changes in Gene Expression in the Cerebral Cortex of Rats After Short- and Long-Term Total Sleep Deprivation," *Sleep* 22(S):113 (1999).
Cirelli et al., "Difference in brain gene expression between sleep and waking as revealed by mRNA differential display and cDNA microarray technology," *J. Sleep Research* 8:44-52 (1999).
Cirelli et al., "Differences in Gene Expression Between Sleep and Waking as Revealed by mRNA Differential Display," *Molecular Brain Research* 56:293-305 (1998).
Cirelli et al., "Differences in gene expression during sleep and wakefulness," *Ann. Med.* 31:117-124 (1999).

(Continued)

*Primary Examiner*—D. L Jones
(74) *Attorney, Agent, or Firm*—McDermott Will & Emery LLP

(57) ABSTRACT

The invention provides a method of identifying a compound that alters vigilance. The method consists of contacting an invertebrate with a candidate compound, evaluating a vigilance property in the contacted invertebrate, and determining if the candidate compound alters the vigilance property in the contacted invertebrate. A candidate compound that alters the vigilance property in the contacted invertebrate is identified as a compound that alters vigilance. The invention also provides a method of identifying a vigilance enhancing compound that modulates homeostatic regulation or a vigilance diminishing compound that modulates homeostatic regulation. The method consists of contacting an invertebrate with a compound that increases or decreases vigilance, and determining the effect of the compound on a homeostatic regulatory property of vigilance. A compound that alters the homeostatic regulatory property is characterized as being a vigilance enhancing compound or a vigilance diminishing compound that modulates homeostatic regulation.

2 Claims, 5 Drawing Sheets

OTHER PUBLICATIONS

Cirelli et al., "Modulations of desynchronized sleep through microinjection of alpha-1-adrenergic agonists and antagonists in the dorsal pontine tegmentum of the cat," *Pflugers Archiv.* 422:273-279 (1992).

Clark, "Genetics Components of Variation in Energy Storage in *Drosphila Melanogaster*," *Evolution* 44:637-650 (1990).

Connolly, "Locomotor activity in *Drosphila* as a Function of Food Deprivation," *Nature* 209:224 (1966).

Cortelli et al., "Fatal familial insomnia: clinical features and molecular genetics," *J. Sleep Res.* 8(S):23-29 (1999).

Dijk et al., "Ageing and the circadian and homeostatic regulation of human sleep during forced desynchrony of rest, melatonin and temperature rhythms," *Journal of Physiology* 516:611-627 (1999).

Dudai, "Inhibitors of Phosphodiesterase Affect Behavioral Plasticity in *Drosophila melanogaster*," *Israel J. Med. Sci.* 15:802 (1979).

Dunkov et al., "Cytochrome P450 gene clusters in *Drosphila melanogaster*," *Mol. Gen. Genet.* 251:290-297 (1996).

Hamblen et al., "Germ-line transformation involving DNA from the period locus in Drosophila melanogester: overlapping genomic fragments that restore circadian and ultradian rhythmicity to per0 and per- mutants," *J. Neurogen.* 3:249-291 (1986).

Hendricks et al., "Rest in *Drosophila* is a Sleep-like State," *Neuron* 25(1):129-138 (2000).

Hintermann et al., "Cloning of an Arylalkylamine N-acetyltransferase (aaNAT1) from *Drosophila melanogaster* Expressed in the Nervous System," *Proc. Natl. Acad. Sci. USA* 93:12315-12320 (1996).

Hoyle, "Learning of leg position by the ghost crab Ocypode ceratophthalma," *Behav. Biol.* 18:147-163 (1976).

Inoue et al., "Behavior-modulating effects of uridine in the *rhinoceros beetle allomyrina-dichotoma*," *Zoological Science* (Tokyo) 3:727-730 (1986). (Abstract only).

Inouée et al., "Behavior-Modulating Effects of Uridine in the Rhinoceros beetle," *Zoological Science* 3:727-729 (1986).

Ishida et al., "Biological Clocks," *Prod. Natl. Acad. Sci. USA* 96:8819-8820 (1999).

Itoyama et al., "Effects of caffeine on mating frequency and pre-couplation and couplation durations in *Drosophila prosaltans*," *Cytobios* 83:245-248 (1995).

Jacobs et al., "Effects of food deprivation on sleep and wakefulness in the rat," *Exp. Neural.* 30:212-222 (1971).

Jouvet, "Sleep and Serotonin: An Unfinished Story," *Neuropsychopham.* 21(2S):24S-27S (1999).

Kaiser et al., "Neuronal correlates of sleep, wakefulness and arousal in a diurnal insect," *Nature* 301:707-709 (1983).

Kandel et al., "A common Presynaptic Locus for the Synaptic Changes Underlying Short-Term Habituation and Sensitization of the Gill-Withdrawal Reflex in Aplysia," *Cold Springs Harb. Symp. Quant. Biol.* 40:465-482 (1976).

Kimoff et al., "Canine model of obstructive sleep apnea: model description and preliminary application," *J. Appl. Physiol.* 76:1810-1817, no date available.

Krishnan et al., "A genetic study of the anesthetic response: Mutants of *Drosophila melanogaster* altered in sensitivity of halothane," *Proc. Natl. Acad. Sci. USA* 87:8632-8636 (1990).

Kuhl et al., "Long-term sensitization training in Aplysia leads to an increase in the expression of BiP, the major protein chaperon of the ER," *J. Cell Biol.* 119:1069-1076 (1992).

Legator et al., "Review of the genetic effects of caffeine," *J. Environ. Sci. Hlth.* 13:135-188 (1979).

McClung et al., "Stereotypic behavioral responses to free-base cocaine and the development of behavioral sensitization in *Drosophila*," *Current Biology* 8:109-112 (1998).

McGinty et al., "dorsal raphe neurons: depression of firing during sleep in cats," *Brain Research* 101:569-575 (1976).

Michaud et al., "Mild insomnia induced by environmental perturbations in the rat a study of this new model and of its possible application in pharmacological research," *Arch. int. Pharmacodyn* 259:93-105 (1982).

Michaud et al., "Mild insomnia induced by environmental perturbations in the rat: a study of this new model and of its possible applications in pharmacological research," *Arch. Int. Pharmacodyn. Ther.* 259:93-105, no date available.

Mizunami et al., "Mushroom Bodies of the Cockroach: Their Participation in Place Memory," *Journal of Comparative Neurology* 402:520-537 (1998).

Nassel, "Histamine in the Brain of Insects: A Review," *Microscopy Research and Technique* 44:121-136 (1999).

Pahl et al., "Signal Transduction From the Endoplasmic Reticulum to the Cell Nucleus," *Physiological Review* 79:683-701 (1999).

Panckeri et al., "Modafinil decreases hypersomnolence in the English bulldog, a natural animal model of sleep-disordered breathing," *Sleep* 19:626-631 (1996).

Perkins et al., "The Drosophila Fos-related Ap-1 protein is a developmentally regulated transcription factor," *Genes Dev.* 4:822-834 (1990).

Phillis et al., "Isolation of mutations affecting neural circuitry required for grooming behavior in *Drosophila melanogaster*," *Genetics* 133:581-592 (1993).

Pompeiano et al., "Immediate-early genes in spontaneous wakefulness and sleep: expression of c-fos and NGFI-A mRNA and protein," *J. Sleep Res.* 3:80-96 (1994).

Quinn et al., "Conditioned Behavior in *Drosophila melanogaster*," *Proc. Natl. Acad. Sci. USA* 71:708-712 (1974).

Rankin et al., "*Caenorhabditis elegans*: a new model system for the study of learning and memory," *Behav. Brain Res.* 37:89-92 (1990).

Rankin et al., "*Caenorhabditis-elegans* a new model system for the study of learning and memory," *Behavioral Brain Research* 37:89-92 (1990).

Sauer et al., "The effects of forced activity on a behavioral sleep sign in honey bees," *Sleep Res. Online* 2(Suppl. 1):217 (1999).

Schwartz et al., "Towards a molecular biology of the suprachiasmatic nucleus: photic and temporal regulation of c-fos gene expression," *Sem. Neurosci.* 7:53-60 (1995).

Shaw et al., "Behavioral and Molecular correlates of Sleep-Like States in *Drosophila melanogaster*," Abstracts of papers presented at the *1999 meeting on Neurobiology of Drosophila, cold Spring Harbor Laboratory* (1999).

Shaw et al., "Correlates of Sleep and Waking in *Drosophila melanogaster*," *Science* 287:1834-1837 (2000).

Shaw et al., "Homeostatic Aspects of the Rest-Activity Cycle in *Drosphila Melanogaster* and Their Molecular Correlates," *Sleep Research Online* 2(Supplement 1):218 (1999).

Shaw et al., "Molecular Correlates of the Rest-Activity Cycle in *Drosphila Melanogaster*," *29th Annual Meeting, Society of Neuroscience* 25, Abstract 459.1 (1999).

Siegel et al., "A function for REM sleep: regulation of noradrenergic receptor sensitivity," *Brain Res. Rev.* 13:213-233 (1988).

Siegel, "Narcolepsy: A Key Role for Hypcretins (Orexins)," *Cell* 98:409-412 (1998).

Stone, "Sleep and Aging in Animals," *Clin. Ger. Med.* 5:363-379 (1989).

Tatusova et al., "Blast 2 Sequences, a new tool for comparing protein and nucleotide sequences," *FEMS Microbiology Letters* 174:247-250 (1999).

Tober, "Effect of Forced Locomotion on the Rest-Activity Cycle of the Cockroach," *Behavioural Brain Res.* 8:351-360 (1983).

Tobler et al., "24-h variation of vigilance in the cockroach *Blaberus*," *J. Sleep. Res.* 1:231-239 (1992).

Tobler et al., "Rest in scorpian—a sleep-like state?," *J. Comp. Physiol. A.* 163:227-235 (1988).

Tobler et al., "Rest in the scorpion—a sleep-like state?," *J. Comp. Physiol.* 163:227-235 (1988). (Duplicate of Reference #76).

Van Gelder et al., "Extent and character of circadian gene expression in *Drosophila melanogaster*: identification of twenty oscillating nRNAs in the fly head," *Current Biology* 5:1424-1436 (1995).

Wong-Riley et al., "Brain Cytochrome Oxidase Subunit Complementary DNAs: Isolation, Subcloning, Sequencing, Light and Electron Microscopic *In Situ* Hybridization of Transcripts, and Regulation by Neuronal Activity," *Neuroscience* 76:1035-1055 (1997).

Xia et al., "Drug Disruption of Short-Term Memory in *Dropophila melanogaster*," *Pharmacology Biochemistry and Behavior* 58:727-735 (1997).

Yanik et al., "The dose-response effects of caffeine on sleep in rats," *Brain Res.* 403:177-180 (1987).

Yehuda et al., "Fatty Acids and Brain Peptides," *Peptides* 19:407-419, no date available.

Yin et al., "Induction of a Dominant negative Creg Transgene Specifically Blocks Long-Term Memory in *Drosophila*," *Cell* 79:49-58 (1994).

* cited by examiner

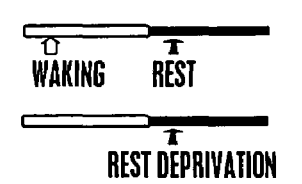
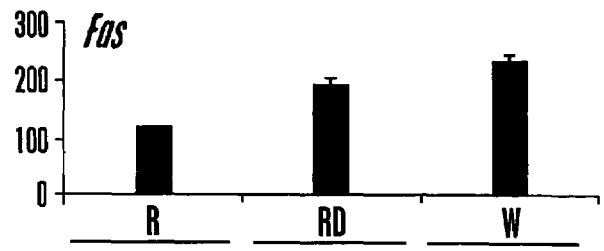
Figure 4A
Figure 4B
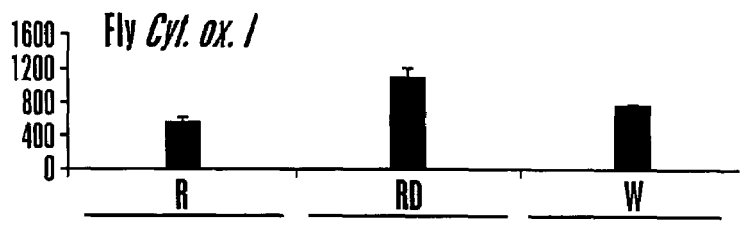
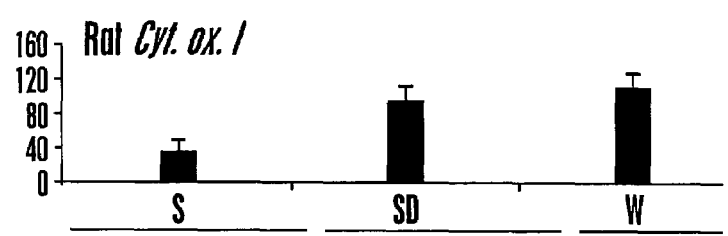
Figure 4C
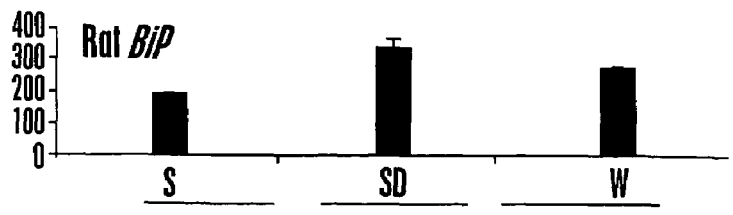
Figure 4D

METHODS FOR IDENTIFYING COMPOUNDS THAT MODULATE VIGILANCE STATES

This application is a continuation of U.S. Ser. No. 09/718,828, filed on Nov. 22, 2000, issued as U.S. Pat. No. 6,730,287, on May 4, 2004, which claims the benefit of, U.S. Provisional Application No. 60/367,372, filed Nov. 24, 1999, which was converted from U.S. Ser. No. 09/449,175, all of which are incorporated herein by reference.

BACKGROUND OF THE INVENTION

Sleep is a naturally occurring, periodic, reversible state of unconsciousness that is ubiquitous in mammals and birds, although its precise function is not known. The importance of sleep is suggested by its homeostatic regulation: the longer an animal is awake, the more it needs to sleep.

In humans, obtaining less than the required number of hours of sleep, particularly over several nights, leads to a decreased ability to retain new information, impaired productivity, altered mood, lowered resistance to infection and an increased susceptibility to accidents. Sleep-related traffic accidents annually claim thousands of lives, and operator fatigue has also been shown to play a contributory role in airplane crashes and other catastrophic accidents.

Besides lifestyle factors, a variety of physiological and psychological disorders can affect sleep patterns. The most common sleep disorder is primary insomnia, or a difficulty in initiating or maintaining sleep, which affects a large percentage of the population at some point in their lives. Other common sleep disorders include hypersomnia, or excessive daytime sleepiness, and narcolepsy, which is characterized by sudden and irresistible bouts of sleep.

Currently available drugs used to modulate vigilance, such as drugs that induce sleep, prolong wakefulness, or enhance alertness, suffer from a number of shortcomings. For example, available sleep-inducing drugs often do not achieve the fully restorative effects of normal sleep. Often such drugs cause undesirable effects upon waking, such as anxiety or continued sedation. Many available drugs that increase vigilance do so with a characteristic "crash" when the effect of the drugs wears off. Furthermore, many of the currently available drugs that modulate sleep and wakefulness are addictive or have adverse effects on learning and memory.

Clearly, there is a need to identify drugs that induce restorative sleep or that increase vigilance, without undesirable side effects. Unfortunately, current methods for screening for such drugs, using mammals, are slow, burdensome and expensive. Thus, there exists a need for improved methods for screening for drugs that modulate sleep and vigilance. The present invention satisfies this need and provides related advantages as well.

SUMMARY OF THE INVENTION

The invention provides a method of identifying a compound that alters vigilance. The method consists of contacting an invertebrate with a candidate compound, evaluating a vigilance property in the contacted invertebrate, and determining if the candidate compound alters the vigilance property in the contacted invertebrate. A candidate compound that alters the vigilance property in the contacted invertebrate is identified as a compound that alters vigilance.

In one embodiment, the vigilance property evaluated is a behavioral property, including activity, latency to sleep or arousal threshold. In another embodiment, the vigilance property evaluated is a molecular property, including expression of one or more vigilance-modulated genes.

The invention also provides a method of identifying a vigilance enhancing compound that modulates homeostatic regulation. The method consists of contacting an invertebrate with a compound that increases vigilance, and determining the effect of the compound on a homeostatic regulatory property of vigilance. A compound that alters the homeostatic regulatory property is characterized as being a vigilance enhancing compound that modulates homeostatic regulation.

Also provided is a method of identifying a vigilance diminishing compound that modulates homeostatic regulation. The method consists of contacting an invertebrate with a compound that decreases vigilance, and determining the effect of the compound on a homeostatic regulatory property of vigilance. A compound that alters the homeostatic regulatory property is characterized as being a vigilance diminishing compound that modulates homeostatic regulation.

BRIEF DESCRIPTION OF THE DRAWINGS

FIG. 2 shows the rest-activity system monitored in 5-day old female flies using the infrared system. FIG. 2A Inset shows rest under constant darkness in control $per^{01}$ flies (open circles) and in rest-deprived $per^{01}$ flies (black squares). FIG. 2B Inset shows a plot of rest during recovery versus activity during rest deprivation.

FIG. 4A shows the three experimental conditions used to evaluate changes in gene expression, waking (W), rest (R) and rest deprivation (RD). White bars indicate the light period, black bars indicate the dark period. The graphs in FIGS. 4B-4D show densitometric analysis of mRNA levels of vigilance-modulated genes evaluated using ribonuclease protection assays. FIG. 4B shows levels of Fas and Cyp4e2 mRNA in flies. FIG. 4C shows levels of Cytochrome oxidase C subunit I mRNA in flies and rats. FIG. 4D shows levels of BiP in flies and rats.

DETAILED DESCRIPTION OF THE INVENTION

Figure 1A:
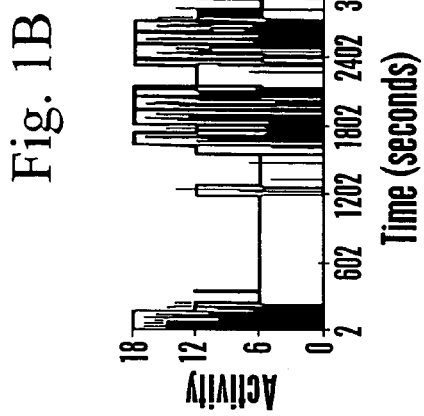
FIG. 1A shows a schematic of the ultrasound activity monitoring system.

The present invention provides methods of rapidly and efficiently identifying compounds that alter vigilance, including compounds that promote sleep, prevent sleep, or increase vigilance. The compounds identified by the methods of the invention can thus be used to treat individuals suffering from psychological, physiological or genetic conditions that deprive them of restorative sleep or that cause excessive sleepiness. These compounds can also be used to prolong wakefulness, such as when it is desired to extend an individual's productivity, or to increase attentiveness, learning or memory.

Sleep in mammals has been defined by several criteria, including electrophysiological and behavioral criteria. Behavioral criteria for sleep include sustained quiescence, increased arousal threshold, and "sleep rebound," or increased sleep or increased sleep intensity following prolonged waking. The criterion of sleep rebound indicates that sleep is under homeostatic control and is thus distinguishable from mere inactivity.

Recently, physiological correlates of sleep in mammals have been extended to the level of gene expression. Molecular screening has revealed that brain levels of mitochondrial enzymes and of several genes implicated in neural plasticity are high during waking and low during sleep (see, for example, (see Cirelli et al., Mol. Brain Res. 56:293 (1998); Cirelli et al., Ann. Med. 31:117 (1999); and Cirelli et al., Sleep 22(S):113 (1999)). Therefore, sleep in mammals can also be characterized by a distinct pattern of gene expression.

Although it is well-known that most organisms exhibit circadian rest-activity cycles, prior to the present invention it was not known that invertebrates exhibit a sleep-like state that is comparable, by behavioral, physiological, developmental, molecular and genetic criteria, to mammalian sleep. This sleep-like state in invertebrates is henceforth referred to as "sleep."

As described herein, invertebrate sleep is very similar, by behavioral criteria, to mammalian sleep. More specifically, as shown in Example I, sleep in an exemplary invertebrate, Drosophila melanogaster, is associated with sustained behavioral quiescence and increased arousal threshold. Additionally, sleep deprivation during the normal sleep period led to a rebound effect comparable to sleep rebound in mammals, indicating that sleep is under similar homeostatic control in invertebrates.

Furthermore, as described herein, sleep in invertebrates is dependent on age, and follows a similar pattern of age dependency as mammalian sleep, indicating that sleep in invertebrates is developmentally regulated. Likewise, sleep remains homeostatically regulated in older invertebrates, as it is in older mammals (see Example II). Additionally, sleep and wake in invertebrates are subject to pharmacological manipulation using compounds that are known to act as stimulants or hypnotics in mammals (see Example III).

Furthermore, of importance to the determination that sleep and wake in invertebrates are truly similar to mammalian sleep and wake, it is also described herein that several classes of genes, and several individual genes, whose regulation is dependent on vigilance state in mammals are similarly regulated in invertebrates (see Example IV). Additionally, as disclosed herein, mutations in genes that regulate sleep in invertebrates affect vigilance properties, including homeostatic regulation of sleep (see Example IV). Likewise, mutations have been identified in mammalian genes that affect sleep, including orexin (see Chemelli et al., Cell 98:437-451 (1999)), indicating that in both invertebrates and mammals, vigilance is under genetic control.

The discovery that invertebrates exhibit sleep and wake states that are similar by behavioral, developmental, pharmacological, genetic and molecular criteria to mammalian sleep and wake, provides a basis for the methods disclosed herein of identifying novel compounds that can be used to modulate vigilance in mammals by screening compounds for their effect on vigilance properties in invertebrates.

The invention provides a method of identifying a compound that alters vigilance. The method consists of contacting an invertebrate with a candidate compound, evaluating a vigilance property in the contacted invertebrate, and determining if the candidate compound alters the vigilance property in the contacted invertebrate A candidate compound that alters the vigilance property in the contacted invertebrate is identified as a compound that alters vigilance.

As used herein, the term "vigilance" is intended to mean the degree or extent to which an organism exhibits sleep or wake behaviors. Thus, the term "altering vigilance" is intended to encompass a change in state from wake to sleep or vice-versa, as well as any increase or decrease in intensity or duration of behaviors associated with a sleep or wake state.

The methods of the invention can be used to identify compounds that either increase or decrease vigilance. A compound that increases vigilance can, for example, cause the animal to wake from sleep, prolong periods of wakefulness, prolong normal latency to sleep, restore normal sleep patterns following sleep deprivation, or enhance beneficial wake-like characteristics, such as alertness, responsiveness to stimuli, energy, and ability to learn and remember. In contrast, a compound that decreases vigilance can, for example, cause an animal to sleep, prolong periods of sleep, promote restful sleep, decrease latency to sleep, or decrease unwanted wake-like characteristics, such as anxiety and hyperactivity.

As used herein, the term "vigilance property" is intended to mean a behavioral, physiological or molecular property in invertebrates that is correlated with mammalian sleep and wake states. As described further below, invertebrates can exhibit a variety of behavioral properties that are closely correlated with mammalian sleep and wake states, including activity, arousal threshold and latency to sleep. Additionally, as described further below, invertebrates can exhibit a variety of molecular properties that are closely correlated with mammalian sleep and wake states, including expression of vigilance-modulated genes. Invertebrates can also exhibit physiological properties that are closely correlated with mammalian sleep, including the frequency, type and intensity of neuronal signals, heart rate, and the like.

Generally, invertebrates exhibit circadian patterns of rest and activity, with most rest occurring during the night in diurnal animals and most activity occurring during the day. In contrast, in nocturnal animals most rest occurs during the day, whereas most activity takes place during the night. Under laboratory conditions, it is possible to regulate the circadian rest-activity cycle by regulating the length of light and dark, and thus establish what are referred to herein as "normal wake periods" and "normal sleep periods." For example, in Drosophila melanogaster subjected to a 12 h:12 h light:dark cycle, the "normal wake period" is the 12 hour light period, whereas the "normal sleep period" is the 12 hour dark period. Those skilled in the art can readily determine or establish normal wake and sleep periods for other invertebrates.

An example of a behavioral vigilance property that can be evaluated in invertebrates is activity during all or part of a normal wake or sleep period. As used herein, the term "activity" is intended to encompass all behavioral activities normally exhibited by that invertebrate including, for example, locomoting, movements of body parts, grooming, eating, and the like, in contrast to "inactivity" or "rest." Activity can be evaluated throughout a normal wake period or throughout a normal sleep period, or both, or evaluated for only part of a normal wake or sleep period, such as for at least 10 minutes, 30 minutes, 1, 2, 4, 6, 8 or 12 hours. Once activity during a normal sleep period or normal wake period is established, those skilled in the art can readily evaluate whether a candidate compound increases or decreases intensity of activity or alters the pattern of activity during all or part of that period.

For certain applications of the method, it will be preferable to evaluate activity following sleep deprivation. As described previously, sleep rebound following sleep deprivation is a characteristic of homeostatically regulated sleep. Thus, by establishing the normal sleep rebound behavior of the invertebrate, those skilled in the art can readily evaluate whether a candidate compound affects the normal homeostatic regulation of sleep.

As used herein, the term "sleep deprivation" refers to depriving the animal of rest. This deprivation is generally for a sufficient period of time during a normal sleep period to result in a detectable decrease in activity, increase in sleep, or increase in intensity of sleep during the subsequeent period, also known as a "sleep rebound" effect. In general, sleep deprivation results from depriving the animal of rest during at least 10%, such as at least 25%, including from 50% to 100% of the normal sleep period.

Any method appropriate for the particular invertebrate can be used to deprive an animal of sleep. As described in Example I, *Drosophila melanogaster* can be sleep-deprived for the entire normal sleep period, using manual or automated physical stimulation, and the amount, pattern and intensity of activity indicative of sleep rebound evaluated (see FIG. 2A). In other organisms, it may be preferable to sleep-deprive the animals using electrical stimulation, noise, or other stimuli, for longer or shorter periods. The time period and method for sleep-depriving an animal can be determined by those skilled in the art for a particular application.

Figure 1B:
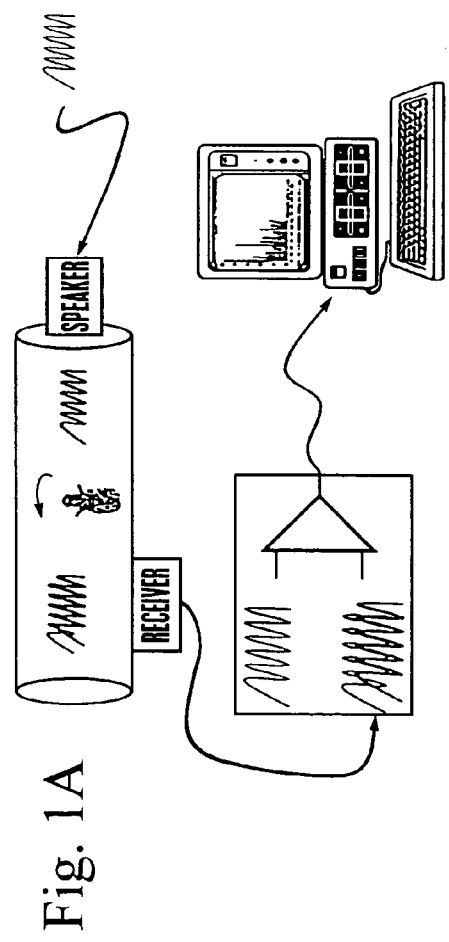
FIG. 1B shows a trial comparing *Drosophila* activity detected by the ultrasound apparatus (gray columns) to three behavioral states scored by a human observer (black lines).
Figure 1C:
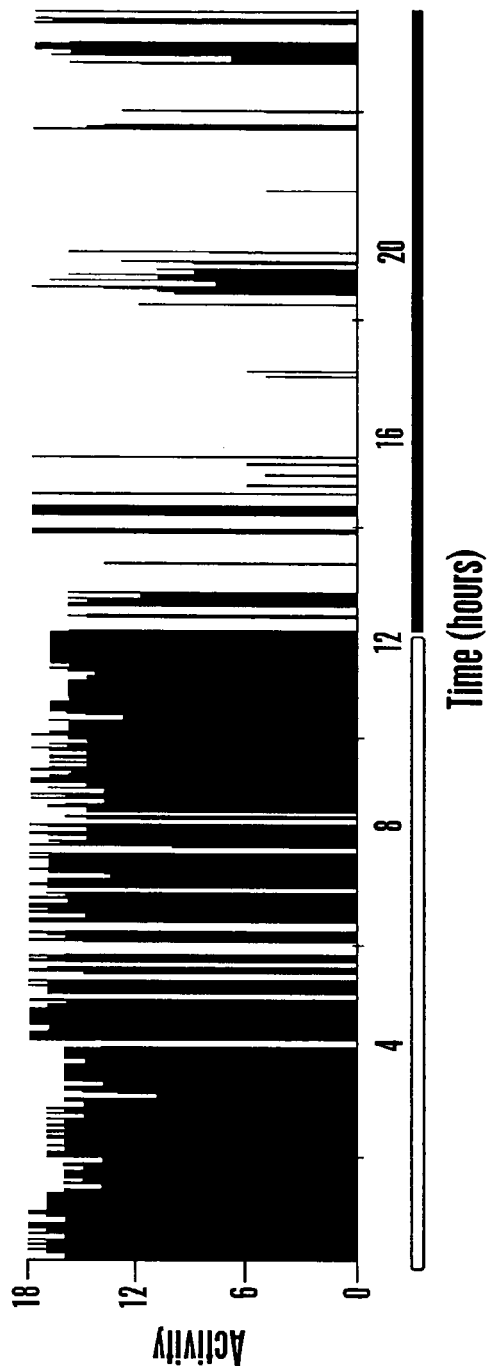
FIG. 1C shows *Drosophila* activity during the light period (horizontal white bar) and the dark period (horizontal black bar).

Various manual and automated assays can be used to evaluate intensity and patterns of activity. For example, activity can be detected visually, either by direct observation or by time-lapse photography. Alternatively, an ultrasound monitoring system can be used, such as the system shown in FIG. 1A and described in Example I, below. Such a system is advantageous in detecting very small movements of the animals' body parts and, as shown in FIG. 1B, the output is closely correlated with visual observations. An example of the activity of *Drosophila melanogaster* during a normal wake period (12 hour light period) and a normal sleep period (12 hour dark period), as evaluated using an ultrasound monitoring system, is shown in FIG. 1C.

As a further example, an infrared monitoring system, such as the infrared *Drosophila* Activity Monitoring System available from Trikinetics (described in M. Hamblen et al., *J. Neurogen.* 3:249 (1986)), can be used. As described in Example I, below, an infrared monitoring system is advantageous when simultaneously evaluating activity in large numbers of invertebrates. An example of the activity of a population of *Drosophila melanogaster* during a normal wake period (12 hour light period) and a normal sleep period (12 hour dark period), as evaluated using an ultrasound monitoring system, is shown in FIG. 1C.

Those skilled in the art can determine an appropriate method to evaluate invertebrate activity in a particular application of the method, depending on considerations such as the size and number of invertebrates, their normal activity level, the intended number of data points, and whether a quantitative or qualitative assessment of activity is desired.

A further example of a behavioral vigilance property that can be evaluated in invertebrates is latency to sleep. As used herein, the term "latency to sleep" refers to the period of time to the first rest bout following the change from the normal wake period to the normal sleep period (ie. from light to dark in diurnal animals, or from dark to light in nocturnal animals). As shown in FIG. 4E, latency to sleep in control *Drosophila melanogaster* was about 40 minutes. If desired, latency to sleep following sleep deprivation can also be established. Once normal latency to sleep, or latency to sleep following sleep deprivation are established for a particular invertebrate, one skilled in the art can evaluate whether a candidate compound increases or decreases this vigilance property.

Another example of a behavioral vigilance property that can be evaluated in invertebrates is arousal threshold. As used herein, the term "arousal threshold" refers to the amount of stimulation required to elicit a behavioral response, such as movement. Any reproducible stimulus can be used to evaluate arousal threshold including, for example, vibratory stimulus, noise, electrical stimulation, heat, or light.

Invertebrates that are in a wake state will exhibit a behavioral response at a lower level of stimulation than invertebrates that are in a sleep state. For example, as described in Example I, below, when subjected to vibratory stimuli of varying intensities, *Drosophila melanogaster* that were in a wake-like state, as determined by activity criteria, responded to low-level stimuli that did not elicit a response in flies that were in a sleep state. Furthermore, an animal that is deeply asleep will exhibit an increased arousal threshold compared to an animal that less deeply asleep. Accordingly, arousal threshold is a measure of sleep versus wake, as well as intensity of sleep. Once normal arousal threshold associated with sleep and wake are established for a particular invertebrate, those skilled in the art can readily evaluate whether a candidate compound increases or decreases this vigilance property.

Other vigilance properties that can be measured in invertebrates include molecular properties correlated with sleep and wake states. As used herein, the term "molecular property" refers to any property that can be evaluated in invertebrate tissues, cells or extracts, including, for example, production or turnover of a second messengers, GTP hydrolysis, influx or efflux of ions or amino acids, membrane voltage, protein phosphorylation or glycosylation, membrane voltage, enzyme activity, protein-protein interactions., protein secretion, and gene expression.

A specific example of a molecular vigilance property that can be evaluated in invertebrates is expression of one or more vigilance-modulated genes. As used herein, the term "expression" is intended to encompass expression at the mRNA or polypeptide level. Accordingly, expression of a vigilance-modulated gene can be evaluated by any qualitative or quantitative method that detects mRNA, protein or activity, including methods described further below. Once the abundance or pattern of expression of vigilance-modulated genes are established for a particular invertebrate, those skilled in the art can readily evaluate whether a candidate compound increases or decreases expression of one or more vigilance-modulated genes.

As used herein, the term "vigilance-modulated gene" refers to a gene whose expression level varies according to vigilance state. For example, the expression level of a vigilance-modulated gene can normally vary by at least about 10%, such as at least 25%, or at least about 50%, including at least about 100%, 250%, 500%, 1000% more between sleep and wake. As described herein, at least about 1% of the transcripts in invertebrates are modulated by vigilance state and, consequently, correspond to vigilance-modulated genes. Therefore, in the methods of the invention one can evaluate expression of at least one vigilance-modulated gene, such as at least 2, 5, 10, 20, 50, 100 or more vigilance-modulated genes. Although not necessary for the practice of the invention, as described below, these genes can be cloned and/or their sequences determined using standard molecular biology procedures.

If desired for a particular application of the method, genes whose expression is normally upregulated in the wake-like state, or genes whose expression is normally upregulated in sleep, or any combination, can be evaluated.

Exemplary vigilance-modulated genes in *Drosophila melanogaster* include a homolog of mammalian Fatty acid synthase (Fas); Cytochrome oxidase C, subunit I; Cytochrome p450 (Cyp4e2); BiP; and arylalkyamine N-acetyl transferase (Dat). Each of these genes was expressed at higher levels during waking than during sleep (see Example IV). In contrast, a gene designated "Rest" was 45% higher during sleep than during rest.

As disclosed herein, there is similarity between vigilance-modulated gene expression in rats and in *Drosophila melanogaster*, both in terms of number and type of genes that are modulated. For example, as described in Example IV, below, Cytochrome oxidase C, subunit I shows a rapid increase in expression during the first few hours of waking in both rats and *Drosophila*. Likewise, expression of a *Drosophila* and a rat Cytochrome P450 were similarly upregulated in waking and sleep deprivation. Therefore, vigilance-modulated genes in invertebrates include homologs of genes whose expression levels vary with the vigilance state of mammals.

A variety of vigilance-modulated genes in rats are described in Cirelli et al., *Mol. Brain Res.* 56, 293 (1998); Cirelli et al., *Ann. Med.* 31:117 (1999); Cirelli et al., *Sleep* 22(S):113 (1999) and include, for example, immediate-early genes, transcription factors and chaperones (e.g. NGFI-A, NGFI-B, Zn-15 related zinc finger, Arc, JunB and IER5); mitochondrial genes (e.g. Cytochrome oxidase C subunit 1, Cytochrome oxidase C subunit IV, NADH dehydrogenase subunit 2, 12S rRNA and F1-ATPase subunit alpha; and other genes, such as neurogranin, bone morphogenetic protein 2, glucose-regulated protein 78, brain-derived neurotrophic factor, interleukin-1β, dendrin, and $Ca^{++}$/calmodulin-dependent protein kinase II (α-subunit) Other vigilance-modulated genes in rats include Cytochrome P450 (Cyp4F5), AA117313, aryl sulfotransferase IV, human breast autoantigen homolog, KIAA313 homolog, and membrane protein E25. Therefore, invertebrate homologs of each of these genes are considered to be vigilance-modulated genes.

Those skilled in the art can determine the extent of identity or similarity between two genes needed to establish that an invertebrate sequence is the homolog of a mammalian vigilance-modulated gene. Generally, homologous genes will encode polypeptides having at least about 25% identity, such as at least about 30%, 40%, 50%, 75% or greater identity across the entire sequence, or a functional domain thereof. Methods for cloning homologs from any invertebrate species, using PCR or library screening, are well known in the art, and are described, for example, in standard molecular biology manuals such as Sambrook et al., *Molecular Cloning: A Laboratory Manual*, Cold Spring Harbor Laboratory, New York (1992) and in Ansubel et al., *Current Protocols in Molecular Biology*, John Wiley and Sons, Baltimore, Md. (1998).

Another example of a molecular vigilance property that can be evaluated in invertebrates is function of one or more vigilance-altering genes. As used herein, the term "vigilance-altering gene" refers to a gene whose expression level can, but does not need to, vary with vigilance state, but whose function influences or is required for inducing or maintaining a vigilance level or a vigilance property. Exemplary functions of a vigilance-altering gene that can be evaluated include transcriptional or translational regulatory activity, and phosphorylation, dephosphorylation, glycosylation or other post-translational modification.

Vigilance-modulated genes and vigilance-altering genes can be identified, or their roles confirmed, by a variety of methods, including genetic methods. For example, animals can be generated or identified with mutations at selected or random loci, and their vigilance properties evaluated in order to determine whether vigilance-modulated or vigilance-altering genes map to these loci. For example, as described in Example IV, below, the gene for arylalkylamine N-acetyl transferase (also known as dopamine acetyltransferase, or Dat) is both a vigilance-modulated gene and a vigilance-altering gene in invertebrates. *Drosophila* homozygous for a naturally-occurring hypomorphic allele of this gene, $Dat^{lo}$, exhibit a sleep rebound following sleep deprivation that is much greater than in wild-type flies, indicating that the Dat gene functions in the homeostatic regulation of sleep. *Drosophila* hemizygous for the $Dat^{lo}$ mutation, generated by crossing homozygotes with *Drosophila* deficient at the Dat locus (Df), exhibit an even more severe sleep rebound effect. Other vigilance modulated genes and vigilance-altering genes can be identified, or their roles confirmed, by similar methods.

As described in Example IV, below, Dopa decarboxylase (Ddc) is a further example of a vigilance-altering gene whose function affects homeostatic regulation of sleep. More specifically, the amount of Ddc enzymatic activity in the invertebrate is directly correlated with the amount of sleep rebound exhibited by the animal following sleep deprivation, with animals severely mutant at the Ddc locus exhibiting less rebound than more mildly affected flies, and mildly affected flies exhibiting less rebound than wild-type flies.

Genetic methods of identifying new vigilance-modulated or vigilance-altering genes that are applicable to a variety of invertebrates are known in the art. For example, the invertebrate can be mutagenized using chemicals, radiation or insertions (e.g. transposons, such as P element mutagenesis), appropriate crosses performed, and the progeny screened for phenotypic differences in vigilance properties compared with normal controls. The gene can then be identified by a variety of methods including, for example, linkage analysis or rescue of the gene targeted by the inserted element. Genetic methods of identifying genes are described for *Drosophila*, for example, in Greenspan, *Fly Pushing: The Theory and Practice of Drosophila Genetics*, Cold Spring Harbor Laboratory Press (1997).

There is a distinction between genes that are modulated by vigilance state and genes that are modulated by circadian rhythms. Thus, a gene that is modulated by vigilance state will have a particular expression level during a normal wake period that is similar to the expression level following sleep deprivation, and a different expression level during a normal sleep period. In contrast, a gene that is modulated by circadian rhythms will have a particular expression level during the light period, and a different expression level during the dark period, independent of the vigilance state of the animal. As shown in Example IV, below, D-fos is an example of a gene whose expression is modulated by circadian rhythm rather than by vigilance state.

Assays to evaluate expression of vigilance-modulated genes can involve sacrificing the animal at the appropriate time, such as during a normal wake period, during a normal sleep period or following sleep deprivation, homogenizing the entire animal, or a portion containing the brain or sensory organs, and extracting either mRNA or proteins therefrom. Alternatively, such assays can be performed in biopsied tissue from the invertebrate.

A variety of assays well known in the art can be used to evaluate expression of particular vigilance-modulated genes, including the genes described above. Assays that detect mRNA expression generally involve hybridization of a detectable agent, such as a complementary primer or probe, to the nucleic acid molecule. Such assays include, for example, Northern or dot blot analysis, primer extension, RNase protection assays, reverse-transcription PCR, competitive PCR, real-time quantitative PCR (TaqMan PCR), and nucleic acid array analysis.

Additionally, constructs containing the promoter of a vigilance-modulated gene and a reporter gene (e.g. β-galactosidase, green fluorescent protein, luciferase) can be made by known methods, and used to generate transgenic invertebrates. In such transgenic invertebrates, expression of the reporter gene is a marker for expression of the vigilance-modulated gene.

Assays that detect protein expression can also be used to evaluate expression of particular vigilance-modulated genes. Such assays generally involve binding of a detectable agent, such as an antibody or selective binding agent, to the polypeptide in a sample of cells or tissue from the animal. Protein assays include, for example, immunohistochemistry, immunofluorescence, ELISA assays, immunoprecipitation, and immunoblot analysis.

Those skilled in the art will appreciate that the methods of the invention can be practiced in the absence of knowledge of the sequence or function of the vigilance-modulated genes whose expression is evaluated. Expression of vigilance-modulated genes can thus be evaluated using assays that examine overall patterns of gene expression characteristic of vigilance state. It will be understood that as these vigilance-modulated genes are identified or sequenced, specific probes, primers, antibodies and other binding agents can be used to evaluate their expression more specifically using any of the above detection methods.

One assay to examine-patterns of expression of vigilance-modulated genes, that does not require prior knowledge of their sequence, is mRNA differential display, which is described, for example, in Cirelli et al., *Mol. Brain Res.* 56:293 (1998) and exemplified in invertebrates in Example IV, below. In such a method, RNA from the animal is reverse-transcribed and amplified by PCR using a particular combination of arbitrary primers. A detectable label, such as an enzyme, biotin, fluorescent dye or a radiolabel, is incorporated into the amplification products. The labeled products are then separated by size, such as on acrylamide gels, and detected by any method appropriate for detecting the label, including autoradiography, phosphoimaging or the like.

Such a method allows concurrent examination of expression of thousands of RNA species, the vast majority of which are expected not to be modulated by vigilance state. However, as described in Example IV, below, there will be a characteristic, reproducible banding pattern associated with vigilance state. It can be readily determined whether a particular candidate compound alters this pattern of gene expression, such as by increasing or decreasing the intensity of vigilance-modulated bands.

A further assay to examine patterns of expression of vigilance-modulated genes is array analysis, in which nucleic acids representative of all or a portion of the genome of the invertebrate, or representative of all or a portion of expressed genes of the invertebrate, are attached to a solid support, such as a filter, glass slide or a chip. Detectably labeled probes, such as cDNA probes, are then prepared from mRNA of an animal, and hybridized to the array to generate a characteristic, reproducible pattern of spots associated with vigilance state. It can be readily determined whether a particular candidate compound alters this pattern of gene expression, such as by increasing or decreasing the intensity of vigilance-modulated spots.

Following identification of patterns of vigilance-modulated gene expression, those skilled in the art can clone the genes, if desired, using standard molecular biology approaches. For example, a vigilance-modulated band identified by differential display can be eluted from a gel and sequenced, or used to probe a library to identify the corresponding cDNA or genomic DNA. Likewise, a vigilance-modulated gene from an array can be identified based on its known position on the array, or cloned by PCR or by probing a library.

Given the teachings described herein that behavioral vigilance properties are closely correlated with molecular vigilance properties, and that behavioral and molecular properties are highly conserved across disparate species, for example, mammals and flies, it is understood that the invention can be practiced using any invertebrate that exhibits at least one behavioral or one molecular vigilance property that is susceptible to evaluation or measurement.

As disclosed herein, *Drosophila melanogaster* is an example of an invertebrate that exhibits a variety of vigilance properties that can be evaluated, including homeostatically regulated activity, arousal threshold, latency to sleep, and expression of vigilance-modulated genes. Those skilled in the art understand that other *Drosophila* species are also likely to exhibit similar vigilance properties, including *D. simulans, D. virilis, D. pseudoobscura D. funebris, D. immigrans, D. repleta, D. affinis, D. saltans, D. sulphurigaster albostrigata* and *D. nasuta albomicans*. Likewise, other flies, including, sand flies, mayflies, blowflies, flesh flies, face flies, houseflies, screw worm-flies, stable flies, mosquitos, northern cattle grub, and the like will also exhibit vigilance properties.

Furthermore, insects other than flies can also exhibit behavioral and molecular vigilance properties. For example, species of cockroach exhibit rest rebound following rest deprivation, as well as a higher arousal threshold correlated with rest (Tobler et al., *Sleep Res.* 1:231-239 (1992)). Thus, the invention can also be practiced with insects such as cockroaches, honeybees, wasps, termites, grasshoppers, moths, butterflies, fleas, lice, boll weevils and beetles.

Arthropods other than insects also can exhibit behavioral and molecular vigilance properties. For example, scorpions exhibit rest rebound following rest deprivation, as well as a characteristic arousal threshold and heart rate associated with rest (Tobler et al., *J. Comp. Physiol.* 163:227-235 (1988)). Thus, the invention can also be practiced using arthropods such as scorpions, spiders, mites, crustaceans, centipedes and millipedes.

Due to the high degree of genetic similarity across invertebrate species, invertebrates other than arthropods, such as flatworms, nematodes (e.g. *C. elegans*), mollusks (e.g. *Aply-*

*sia* or *Hermissenda*), echinoderms and annelids will exhibit behavioral and molecular properties correlated with vigilance state, and can be used in the methods of the invention.

Those skilled in the art can determine, using the assays described herein, whether a particular invertebrate exhibits behavioral or molecular properties correlated with vigilance state and, therefore, would be applicable for use in the methods of the invention. The choice of invertebrate will also depend on additional factors, for example, such as the availability of the animals, the normal activity levels of the animals, the availability of molecular probes for vigilance-modulated genes, the number of animals and compounds one intends to screen, the ease and cost of maintaining the animals in a laboratory setting, the method of contacting and type of compounds being tested, and the particular property being evaluated. Those skilled in the art can evaluate these factors in determining an appropriate invertebrate to use in the screening methods.

For example, if it is desired to evaluate molecular properties in the methods of the invention, an invertebrate that is genetically well-characterized, such that homologs of vigilance-modulate genes are known or can be readily determined, may be preferred. Thus, appropriate invertebrates in which to evaluate molecular properties of vigilance can include, for example, *Drosophila*, and *C. elegans*. If it desired to evaluate behavioral properties in the methods of the invention, an invertebrate that exhibits one or more behavioral properties now known to be consistent with sleep, such as fruit flies, cockroaches, honeybees, wasps, moths, mosquitos, scorpions, may be preferred.

As disclosed herein, invertebrate sleep exhibits an age-dependence similar to mammalian sleep. Therefore, it may be desirable to practice the methods of the invention using invertebrates of different ages so as to identify compounds that alter vigilance in the very young or very old. Such compounds can be tailored for use in pediatric or geriatric patients.

As also disclosed herein, invertebrate sleep patterns differ between females and males. Therefore, it may be desirable to practice the methods of the invention using invertebrates of both genders separately to identify compounds appropriate for use in females, males, or both females and males.

If desired, invertebrates that contain mutations of varying degrees of severity in vigilance-altering genes can be used in the screening methods described herein, and compounds identified that correct these defects. In such screens, a vigilance property is evaluated in mutant invertebrates and in normal invertebrates. A compound that alters the vigilance property in the mutant invertebrate to a level or amount more similar to the property in the normal animal can thus be identified. For example, a screen can be conducted in a *Drosophila* that is mutant at the Dat locus or the Ddc locus, both of which, as shown in Example IV, alter, in different directions, the amount of sleep rebound exhibited by the animal following sleep deprivation. Accordingly, a compound that alters homeostatic regulation of sleep can be identified as a compound that restores more normal sleep rebound in a Dat or a Ddc mutant animal. Animals mutant in other vigilance-modulated or vigilance-altering genes can similarly be identified or generated, and used to identify compounds that affect a particular function implicated in vigilance (e.g. neurotransmitter synthesis or degradation), or a particular property of vigilance, including a homeostatically regulated property of vigilance.

The methods of the invention are practiced by contacting an invertebrate with a candidate compound, and evaluating a vigilance property. Appropriate invertebrates, candidate compounds and vigilance properties to evaluate for various applications of the method have been described above. As used herein, the term "contacting" refers to any method of administering a candidate compound to an invertebrate such that the compound, or a metabolite thereof, is introduced into the invertebrate in an effective amount so as to act on its nervous system.

Exemplary methods of contacting an invertebrate with a candidate compound include feeding the compound to the animal, topical administration of the compound, administration by aerosol spray, immersion of the animal in a solution containing the compound, and injection of the compound. An appropriate method of contacting an invertebrate with a compound can be determined by those skilled in the art and will depend, for example, on the type and developmental stage of the invertebrate, whether the invertebrate is sleeping or awake at the time of contacting, the number of animals being assayed, and the chemical and biological properties of the compound (e.g. solubility, digestibility, bioavailability, stability and toxicity). For example, as shown in Example IV below, *Drosophila melanogaster* can be contacted with stimulants or hypnotics by dissolving the drugs in fly food and providing the food to the flies.

A "candidate compound" used to contact the invertebrate can be any molecule that potentially alters vigilance. A candidate compound can be a naturally occurring macromolecule, such as a peptide, nucleic acid, carbohydrate, lipid, or any combination thereof, or a partially or completely synthetic derivative, analog or mimetic of such a macromolecule. A candidate compound can also be a small organic or inorganic molecule, either naturally occurring, or prepared partly or completely by synthetic methods. If desired, a candidate compound can be combined with, or dissolved in, an agent that facilitates uptake of the compound by the invertebrate, such as an organic solvent (e.g. DMSO, ethanol), aqueous solvent (e.g. water or a buffer), or food.

A candidate compound can be tested at a single dose, or at a range of doses. It is expected that the effects on properties correlated with vigilance will be dose dependent, as demonstrated with caffeine and hydroxyzine in Example III, below. Appropriate concentrations of candidate compound to test in the methods of the invention can be determined by those skilled in the art, and will depend on the chemical and biological properties of the compound and the method of contacting. Exemplary concentration ranges to test include from about 10 µg/ml to about 500 mg/ml, such as from about 100 µg/ml to 250 mg/ml, including from about 1 mg/ml to 200 mg/ml.

The number of different compounds to screen in the methods of the invention can be determined by those skilled in the art depending on the application of the method. For example, a smaller number of candidate compounds would generally be used if the type of compound that is likely to alter vigilance is known or can be predicted, such as when derivatives of a lead compound are being tested. However, when the type of compound that is likely to alter vigilance is unknown, it is generally understood that the larger the number of candidate compounds screened, the greater the likelihood of identifying a compound that alters vigilance. Therefore, the methods of the invention can employ screening individual compounds separately or populations of compounds including small populations and large or diverse populations, to identify a compound that alters vigilance.

The appropriate time and duration to administer the compound can be determined by those skilled in the art depending on the application of the method. For example, it may be desirable to administer a compound at the beginning or end of the normal wake or sleep period, continuously throughout a normal wake or sleep period, or prior to, during, or after sleep deprivation, depending on the vigilance property being evaluated and the desired effect of the compound. As exemplified in Example III, below, compounds that either increase or decrease vigilance can be administered in the last hour of the normal wake period, and their effect on activity during the next sleep period or on latency to sleep can be readily observed.

Methods for producing libraries of candidate compounds to use in the methods of the invention, including chemical or biological molecules such as simple or complex organic molecules, metal-containing compounds, carbohydrates, peptides, proteins, peptidomimetics, glycoproteins, lipoproteins, nucleic acids, antibodies, and the like, are well known in the art. Libraries containing large numbers of natural and synthetic compounds also can be obtained from commercial sources.

Following contacting the invertebrate with the candidate compound, any of the vigilance properties described above can be evaluated, and a determination made as to whether the compound alters, such as increases or decreases, the vigilance property compared to a baseline or established value for the property in an untreated control. Such a compound will similarly alter vigilance in mammals. However, it will be understood that the efficacy and safety of the compound in laboratory mammals can be further evaluated before administering the compound to humans or veterinary animals. For example, the compound can be tested for its maximal efficacy and any potential side-effects using several different invertebrates or laboratory mammals, across a range of doses, in a range of formulations, and at various times during the normal sleep and wake periods.

Additionally, a compound that alters vigilance can be tested for its effects on one or more additional vigilance properties in order to determine its most effective application in therapy. For example, it may be desirable to determine whether a compound that increases vigilance does so without significantly altering latency to sleep when the effect of the compound wears off. Such a compound would be an improvement over many of the currently known vigilance-enhancing drugs that cause a characteristic "crash" afterwards. It may also be desirable to determine whether the compound that alters vigilance does so without a compensatory sleep rebound effect.

Therefore, once a compound is identified that alters a desirable vigilance property, the methods of the invention can be used to determine other vigilance characteristics of the compound. Such other characteristics can be assessed either simultaneously with the initial screen, or alternatively they can be assessed in or more separate screens to identify or characterize other vigilance properties of the compound. For example, a vigilance altering compound identified that promotes sleep can be further assessed to determine whether that compound additionally reduces arousal threshold to normal sleep levels, while preserving the ability of the animal to be wakened normally, and with subsequent normal wake-like behaviors. Such a compound would be an improvement over many of the currently available sleep-inducing drugs, which may not promote truly restorative sleep or normal function on awakening. Similarly, a vigilance altering compound identified that promotes wakefulness can be further assessed, as described above, to determine whether that compound additionally reduces the rate or extent of the wake-sleep transition, or "crash," following the vigilance enhancing effects of the compound.

The methods of the invention are therefore applicable for screening and identifying compounds that exhibit preferred vigilance altering effects as well as for identifying compounds that exhibit a combination of preferred vigilance altering effects to yield optimal vigilance altering compounds. Such optimal vigilance altering compounds can be identified which combine preferred effects on vigilance levels together with maintaining some or all hemostatic regulatory properties of vigilance.

As used herein, "homestatic regulatory properties of vigilance" or "homeostatic regulatory properties" is intended to mean those vigilance properties that are compensatory changes in vigilance resulting from, or correlating with, the quantity or quality of vigilance from a previous time period. Homeostatic regulatory properties are therefore vigilance properties when viewed in light of the vigilance state of a previous period. Such properties include, for example, vigilance properties such as sleep rebound, wake period, latency to sleep, the rate of the sleep-wake transition, alertness or drowsiness when there has been a corresponding and opposite change in vigilance in the immediate, prior period, or when there has been a correlative effect in the immediate, prior period.

For the specific homeostatic regulatory property referred to as sleep rebound, prolonged or more intense sleep periods occur as a compensatory change to prior increases in vigilance periods. For the remaining homeostatic regulatory properties specifically exemplified above, such properties are, for example, compensatory changes due to correlative effects in the prior period. For example, the transition rate between wake and sleep states will be correspondingly increased or decreased depending on the amount and quality of the previous wake or sleep vigilance state. Similarly, an animal will be more alert following a more restful period and will be more drowsy following a less restful period. Such compensatory vigilance states arise from the quality and nature of vigilance state of the previous time period. Homeostatic regulatory properties of vigilance other than those described above also exist and are well known to those skilled in the art.

Preferred or optimal vigilance altering compounds can be identified using the methods of the invention which exhibit, for example, predetermined effects on the magnitude of vigilance levels or on the period and duration of the effect. For example, vigilance altering compounds can be identified that either increase or decrease vigilance levels in small or large increments or to a specified degree. Vigilance altering compounds similarly can be identified that increase or decrease vigilance levels to a maximum amount allowable without affecting other vital or relevant physiological processes. Preferred or optimal compounds also can be selected that modulate the duration of the vigilance altering effect for a predetermined period, including maximal durations, without adversely affecting other vital or relevant physiological processes.

Compounds exhibiting one or more combinations of the above effects can similarly be identified using the methods of the invention. A specific example of one such preferred or optimal combination is a compound that alters vigilance, either by increasing or decreasing vigilance, to its maximal extent, but for a short and specified time. Another example is a compound that results in small alterations in vigilance levels but exhibits a relatively prolonged, and predetermined duration of the effect. Vigilance altering compounds exhibiting other combinations of preferred or optimal vigilance effects can similarly be selected using the methods of the invention, given the teachings and descriptions herein.

Additionally, preferred or optimal vigilance altering compounds can be identified using the methods of the invention which modulate, for example, one or more homeostatic regulatory properties of vigilance following a prior perturbation in vigilance levels or periods. For example, vigilance altering compounds can be identified that modulate the sleep rebound, wake period, latency to sleep, the rate of the sleep-wake transition, alertness or drowsiness. Vigilance altering compounds can be identified, for example, that increase or decrease the period or amount of sleep rebound following prolonged periods of increased vigilance. Similarly, vigilance altering compounds can be identified, for example, that increase or decrease the period or amount of wake period as well as the level of vigilance following prolonged periods of sleep. Such compounds can be preferred because they increase the animal's alertness and therefore decrease lethargic periods during the wake state. Finally, vigilance altering compounds can be identified that, for example, decrease the rate of the wake-to-sleep transition so as to prevent a crash following prolonged waking periods as well as increase the rate of the sleep-to-wake transitions so as to achieve normal levels of vigilance following prolonged or induced periods of sleep.

Vigilance altering compounds exhibiting one or more combinations of the above modulatory effects on homeostatic regulatory properties can similarly be identified using the methods of the invention. One specific example is a compound that prevents or reduces sleep rebound to a specified extent and maintains normal vigilance levels following prolonged wake periods. Another specific example is a compound that increases the rate of the sleep-to-wake transition while also preventing lethargic periods during the wake state following prolonged or induced sleep.

Likewise, the methods of the invention are also applicable to identifying compounds that maintain or mimic, for example, one or more homeostatic regulatory properties following a prior perturbation. For example, it can be desirable to maintain or induce normal homeostatic regulatory properties following prior preturbation of vigilance levels or periods. In such instances, the methods of the invention can be used to identify compounds that cause such effects following a prior modulation of vigilance.

Finally, preferred or optimal vigilance altering compounds can be identified using the methods of the invention which exhibit combinations, including optimal combinations, of one or more preferred vigilance altering effects and modulation or maintenance of one or more homeostatic regulatory properties of vigilance. For example, vigilance altering compounds can be identified that induce specific magnitudes or durations of vigilance levels and which alter homeostatic regulatory properties following the induced changes in vigilance levels. One specific example, is a compound that maximally increases vigilance levels over prolonged periods without a subsequent sleep rebound effect. Alternatively, such a vigilance increasing compound can also result in little or no crash following the prolonged wake period. Another example is a compound that decreases vigilance, such as induces restful sleep states, for a predetermined period without a lethargic vigilance states following the sleep period. Similarly, vigilance altering compounds can be identified that induce specific magnitudes or durations of vigilance levels and which alter homeostatic regulatory properties simultaneously with the induced changes in vigilance levels. Compounds exhibiting various other combinations of vigilant altering effects and modulation, or maintenance, of homeostatic regulatory properties can similarly be identified using the method and teachings described herein.

Therefore, the invention allows the identification of compounds that alter vigilance levels and modulate or maintain homeostatic regulatory properties of vigilance. Such compounds can be identified in the initial screen, or alternatively, such compounds can be identified step-wise by first identifying compounds that alter vigilance and subsequently determining whether such identified compounds affect homeostatic regulatory properties of vigilance, such as sleep rebound and latency to sleep. Similarly, compounds can be identified either in the initial screen or in step-wise procedures that alter vigilance properties and are devoid of deleterious side-effects, such as a precipitous crash after the drug wears off or lack of restfulness following drug induced sleep. Therefore, the methods of the invention are applicable for identifying compounds that alter vigilance in mammals, as well as to identifying compounds that alter vigilance levels with concomitant homeostatic regulatory properties. Similarly, the methods of the invention are also applicable to identifying compounds that alter vigilance in mammals that are devoid of deleterious and unwanted side-effects.

Compounds identified by the methods of the invention as compounds that alter vigilance can also have an effect on neuronal plasticity, or the ability to learn and form memories. Learning is not possible during sleep in mammals, whereas learning and memory are positively associated with the level of vigilance during waking. Thus, by increasing vigilance, it is also possible to increase learning and memory. Accordingly, in one embodiment, the invertebrate is contacted with a candidate compound, a vigilance property is evaluated, and learning or memory is also evaluated.

A variety of assays are known in the art that can be used to evaluate learning and either short-term or long-term memory in invertebrates, including habituation and sensitization assays, and conditioning assays. Habituation refers to a decrease, and sensitization refers to an increase, in a behavioral response on repeated presentation of the same stimulus, and can be considered rudimentary forms of learning. Exemplary habituation assays that can be readily adapted for use in a variety of invertebrates are described, for example, for *C. elegans* in Rankin et al., *Behav. Brain Res.* 37:89-92 (1990); for *Drosophila* in Boynton et al., *Genetics* 131:655-672 (1992); and for *Aplysia* in Kandel et al., *Cold Spring Harb. Symp. Quant. Biol.* 40:465-482 (1976).

Classical (Pavlovian) conditioning is an accepted behavioral paradigm for learning and memory. In an exemplary conditioning assay, invertebrates can be exposed to two different stimuli, such as two odorants or two colors of light, one of which is associated with negative reinforcement, such as an electric shock. The animals are then removed and tested in a new apparatus, similar to the training arrangement but without reinforcement. Avoidance behavior is scored as learning, and retention time of the learned behavior is scored as memory. Exemplary conditioning assays that can be readily adapted for use in a variety of invertebrates are described, for example, for *Drosophila* in Quinn et al., *Proc. Natl. Acad. Sci. USA* 71:708-712 (1974); for cockroach in Mizunami et al., *J. Comp. Neruol.* 402:520-537 (1998); and for crab in Hoyle, *Behav. Biol.* 18:147-163 (1976).

It is understood that modifications which do not substantially affect the activity of the various embodiments of this invention are also included within the definition of the invention provided herein. Accordingly, the following examples are intended to illustrate but not limit the present invention.

EXAMPLE I

Behavioral Correlates of Sleep in *Drosophila*

This example shows that *Drosophila* exhibits sleep that is similar to mammalian sleep, as evidenced by the main behavioral criteria for sleep, namely sustained behavioral quiescence (rest), increased arousal threshold, and increased sleep following prolonged waking (homeostatic regulation).

In order to monitor fly behavior, five-day old virgin female Canton-S *Drosophila melanogaster* were cultured at 25° C., 50-60% humidity, 12 hr:12 hr light:dark cycle, on brewer's yeast, dark corn syrup and agar food, following procedures modified from J. Bennett and D. L. van Dyke, *Dros. Inform. Serv.* 46:160 (1971). Continuous, high-resolution measurement of fly behavior was achieved using an ultrasound activity monitoring system shown in FIG. 1A. Briefly, a 44 kHz standing wave was passed across an independent enclosure containing a single fly. An integrated circuit sampled a portion of each wave as a function of the transmit signal and compared it to the output from the receive signal for the same time-window. When the fly moved its mass within the field, it perturbed the standing wave and the resulting difference was counted as a movement. The output was sampled by a PC at 200 Hz, the data were summed in 2-sec bins and stored for later processing. This system detects very small movements in *Drosophila*'s behavioral repertoire, including fine movements of the head, wings, and limbs.

In order to validate the output of the ultrasound activity monitoring system, five behaviors were visually scored in 2-sec bins by an observer blind to the output of the ultrasound system on 18 independent trials for a total of 8 h. The correspondence rates for specific states were as follows: Locomoting=99%, Inactive=97%, Grooming anterior limbs=94%, Grooming posterior limbs=98%, and Eating=97%. This correspondence rate is similar to that found between measures of activity and polysomnography in humans. A representative validation trial lasting 60 min is shown in FIG. 1B, and indicates that the ultrasound output and visual observation are in good agreement.

As shown in FIG. 1C, using the ultrasound activity monitoring system, female flies maintained on a 12:12 light dark cycle were active throughout the light period (horizontal white bar) and exhibited few periods of sustained inactivity. In contrast, during the dark period (horizontal black bar) there were extended bouts of quiescence. Based on pilot studies, rest was defined as uninterrupted behavioral quiescence lasting for at least 5 min. Greater than 90% of rest occurred during the dark period, as shown in FIG. 1C.

To monitor rest-activity patterns in large numbers of flies, an infrared *Drosophila* Activity Monitoring System was used (Trikinetics; described in M. Hamblen et al., *J. Neurogen.* 3:249 (1986)). To validate the system, flies were visually monitored for a total of 17.75 h (n=7). The number of times the fly crossed the infrared beam was counted in 5-minute bins. Flies were awake but did not cross the beam in 5 out of 213 bins (miss rate=2.35%). The results obtained with the infrared activity monitoring system demonstrated robust circadian organization of activity and showed good correspondence with the ultrasound monitoring system.

In order to determine whether periods of rest are associated with increased arousal thresholds, flies were subjected to vibratory stimuli of increasing intensity (0.05 g, 0.1 g, and 6 g). In these experiments, flies were placed in glass tubes (65 mm in length, 5 mm I.D.) maintained on a hard plastic platform above a Grass speaker. The output of the speaker was controlled via a Beckman signal generator and the resulting vibration of the platform was measured with an accelerometer. Each fly received a stimulus each hour (total of 8 stimuli) of constant intensity. The behavioral state at the time of stimulus delivery and the ensuing response were videotaped and scored off-line.

Flies that had been behaviorally awake readily responded to intensities of 0.05 g and 0.1 g (90% of trials). Flies that had been behaviorally quiescent for 5 minutes or more rarely showed a behavioral response to these stimuli (~20% of trials; $p<0.001$, $\chi^2$) However, when the intensity of the stimulus was increased to 6 g, all flies quickly responded regardless of behavioral state ($p>0.1$, $\chi^2$).

These results indicate that, like sleep in mammals, sustained periods of quiescence in *Drosophila* are characterized by increased arousal thresholds.

Figure 2A:
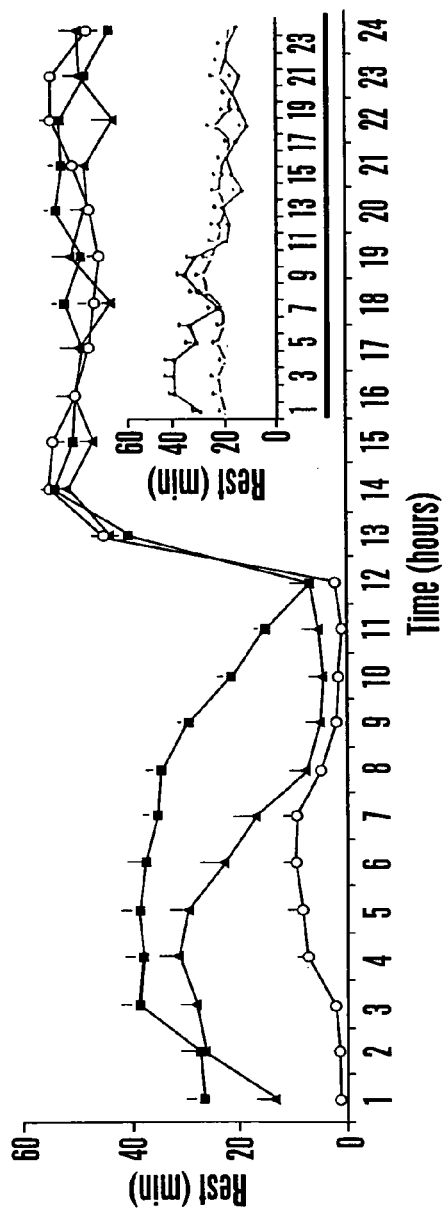
FIG. 2A shows amount of rest under base-line conditions (open circles), following manual rest-deprivation during the dark period (black squares), and following automated rest-deprivation during the dark period (gray triangles).

It was next investigated whether the amount of rest in *Drosophila* is homeostatically regulated. Under baseline conditions the amount of rest during the light period was quite low (FIG. 2A, open circles). Flies (n=24) were deprived of rest individually by gentle tapping of their containers at rest onset (about 4 stimuli/min) for 12 h during the dark period. Efforts were made to avoid disturbing the flies if they were eating or grooming. During the first 12 h of the following light period, rest-deprived flies (FIG. 2A, black squares; $p<0.001$, Wilcoxon signed-ranks test for matched pairs) exhibited a seven-fold increase in rest compared to baseline.

Additionally, an automated system was used to rest-deprive large numbers of flies. Only flies that were active (indicated by the number of infrared crossings) for at least 66% of the light period and inactive (no infrared crossings) for at least 66% of the dark-period were studied. Rest deprivation was achieved by placing glass tubes, containing individual flies, into a cylinder that was rotated in a hybridization oven (Hybaid) at 10 revolutions/minute. At the nadir of the arc the tubes would be carried to the apex and dropped 2.5 cm. Note that flies were not forced to walk throughout each cycle.

Automated rest deprivation for 12 h during the dark period resulted in a three-fold increase in rest over baseline values during the first 6 h of the following light period (mean of 10 independent experiments, n=286, FIG. 2A, gray triangles; all $z>3.1$, $p<0.001$). In the first 24 h following manual rest deprivation, flies recovered 50% of the rest that was lost, a value comparable to the sleep rebound seen in mammals following short-term sleep deprivation.

To investigate whether the homeostatic regulation is separable from circadian factors, $per^{01}$ mutant flies, which are arrhythmic under constant darkness, were examined. Under constant darkness, $per^{01}$ flies had the same amount of rest as under light-dark conditions ($p>0.5$), but the amount of rest was evenly distributed across the 24 hours (open circles). Twelve hours of automated rest deprivation in constant darkness resulted in a significant increase in rest during the first 6 h of recovery (black squares) compared to baseline (n=25, $p<0.001$). Since rest is evenly distributed in $per^{01}$ flies, rest deprivation eliminated only about 50% of daily rest, compared to 90% in wild-type flies.

Figure 2B:
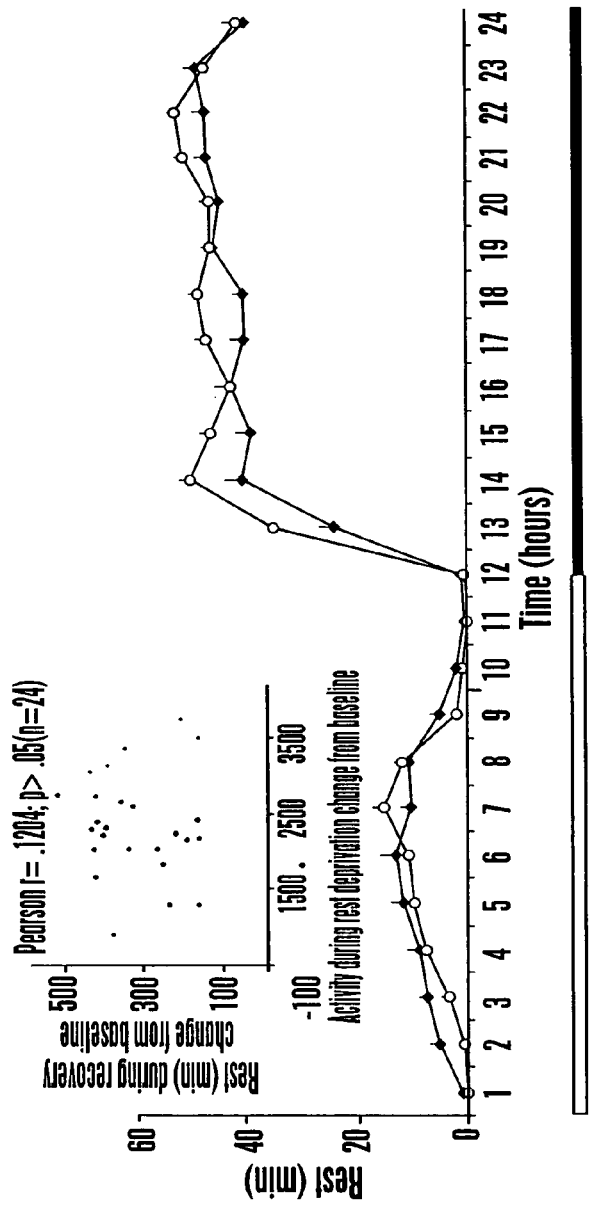
FIG. 2B shows amount of rest under base-line conditions (open circles) and following automated rest-deprivation during the light period (gray triangles).

Recordings with the ultrasound system showed that the rest rebound after deprivation was characterized by actual immobility and not simply an increase of stationary waking activities, such as eating or grooming, that may result in reduced infrared beam crossing. Moreover, the amount of activity during the deprivation was not correlated with the size of the rest rebound, indicating that the increase in rest was not due to levels of prior activity (FIG. 2B, inset). Consistent with this, when flies were stimulated in the apparatus for 12 h during the light period, rest not only failed to increase, but was actually reduced by 16+/−4% during the first 6 h of recovery (FIG. 2B, compare gray diamonds (rest deprived) with open circles (baseline)). Thus, the increase in rest is not due to physical exhaustion induced by forced activity.

Additional controls were used to validate the infrared system. Flies deprived of food for 12 h during the dark period and given food during the following light period showed no change in the number of infrared crossings. This result indicated that eating was not miscoded as rest. Food deprivation has been shown to increase activity in *Drosophila* (Connolly, *Nature* 209:224 (1966)) and waking in mammals (Jacobs et al., *Exp. Neural.* 30:212 (1971)). It was determined that food deprivation for 1 day increased waking by 50% in *Drosophila*. In addition, dusting flies with Reactive Yellow, as described in Phillis et al., *Genetics* 133:581 (1993), increased grooming behavior by 72% but did not reduce the number of infrared crossings. This result indicated that grooming was not miscoded as rest.

In additional experiments it was determined that male flies obtain 70% of their daily rest during the dark period and exhibit an additional rest peak between 03.00 and 07.00 during the light period. Rest deprivation using the automated system revealed that both nighttime rest and rest during the day are homeostatically regulated.

These results indicate that rest in *Drosophila*, like sleep in mammals, is under homeostatic control.

EXAMPLE II

Age-Dependence of Sleep in *Drosophila*

This example shows that *Drosophila* sleep, like mammalian sleep, exhibits age dependence. This example also shows that homeostatic regulation of sleep is preserved in older flies.

In mammals, sleep is prominent in the very young, stabilizes during adolescence and adulthood, and declines during old age (see Stone, *Clin. Ger. Med.* 5:363 (1989); Bliwise, in *Principles and Practice of Sleep Medicine*, Kryger et al. Eds. (Saunders, Philadelphia, $2^{nd}$ ed., 1994), chap. 3; Dijk et al., *J. Physiol.* 516:611 (1999)). To determine whether sleep in *Drosophila* follows a similar pattern, *Drosophila* rest was assayed at various days after eclosion using the infrared system.

Figure 3A:
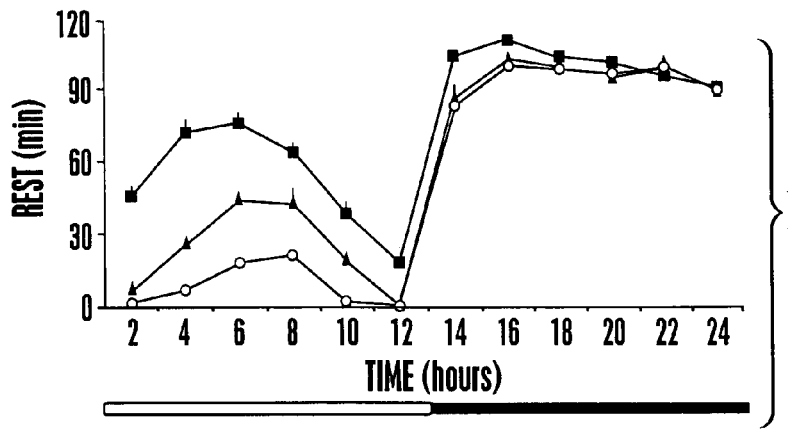
FIGS. 3A and 3B show rest as a function of *Drosophila* age for a 24-hour period. Rest during the light period (horizontal white bar) and the dark period (horizontal black bar) for flies 1 day after eclosion (black squares), 2 days after eclosion (gray triangles), 3 days after eclosion (open circles), 16 days after eclosion (gray diamonds), and 33 days after eclosion (black circles) is shown.
Figure 3B:
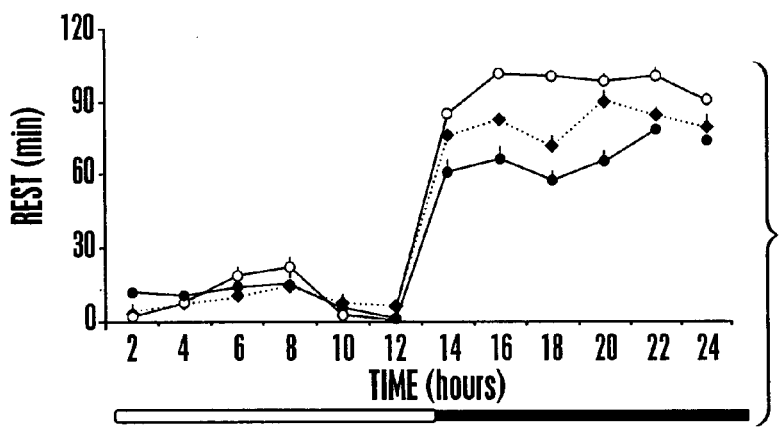

As shown in FIG. 3A, on the first full day after eclosion (black squares) rest was pronounced, decreased on day 2 (gray triangles), and reached stable adult values by day 3 (open circles; $p<0.001$; ANOVA, Bonferroni correction). As shown in FIG. 3B, as the flies aged the amount of rest during the night began to decline (gray diamonds, 16 days of age) and was significantly below that found in young adults (open circles, 3 days of age) by 33 days of age (black circles, $p<0.001$).

These results indicate that rest in *Drosophila* follows a similar age-dependent pattern as sleep in mammals.

Several studies indicate that the homeostatic regulation of sleep is preserved in older humans (see Stone, *Clin. Ger. Med.* 5:363 (1989); Bliwise, in *Principles and Practice of Sleep Medicine*, Kryger et al. Eds. (Saunders, Philadelphia, $2^{nd}$ ed., 1994), chap. 3; Dijk et al., *J. Physiol.* 516:611 (1999)). When 33 day old flies were deprived of rest they exhibited a rest rebound which was similar to that seen in young flies.

These results indicate that homeostatic regulation of rest is preserved in older flies, as it is in older mammals.

EXAMPLE III

Pharmacological Modulation of Sleep in *Drosophila*

This example shows that pharmacological compounds that modulate mammalian vigilance level also modulate fly vigilance level.

Sleep in mammals is modulated by several classes of drugs that act as stimulants or hypnotics. For example, caffeine increases wakefulness and motor activity, while antihistamines reduce sleep latency (Yanik et al., *Brain Res.,* 403:177 (1987)). While the mutagenic effects of caffeine in the fly are well-studied (e.g. Legator et al., *J. Environ. Sci. Hlth.* 13: 135 (1979); Dudai, *Israel J. Med. Sci.* 15:802 (1979); Itoyamaet al., *Cytobios.* 83:245 (1995); Nassel, *Microsc. Res. Tech.* 44:121 (1999)), little is known about its behavioral effects.

Figure 3C:
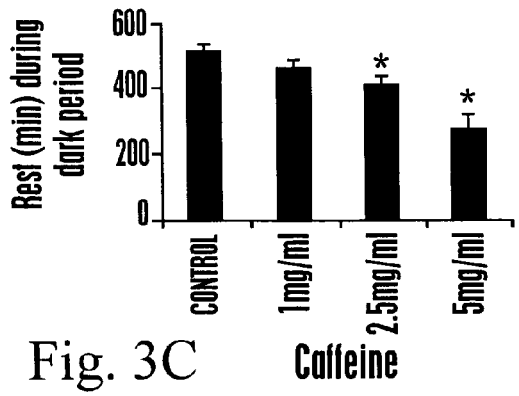
FIG. 3C shows rest during dark period in *Drosophila* given the indicated doses of caffeine beginning in the final hour of the light period.

Drugs (caffeine or hydroxyzine) dissolved in food were continuously available to flies beginning in the final hour of the light period. As shown in FIG. 3C, when flies were given caffeine, the amount of rest during the dark period decreased in a dose-dependent fashion (n=36/dose, *, $p<0.0001$) and motor activity increased.

Figure 3D:
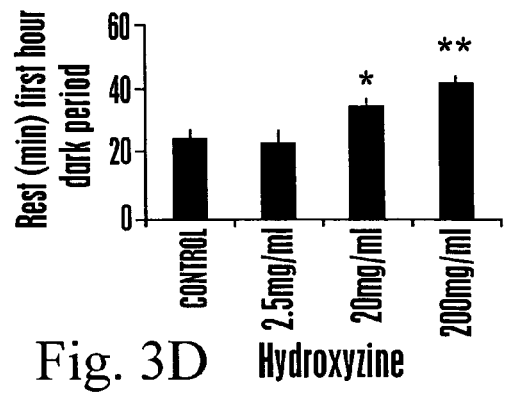
FIG. 3D shows rest in the first hour of the dark period.
Figure 3E:
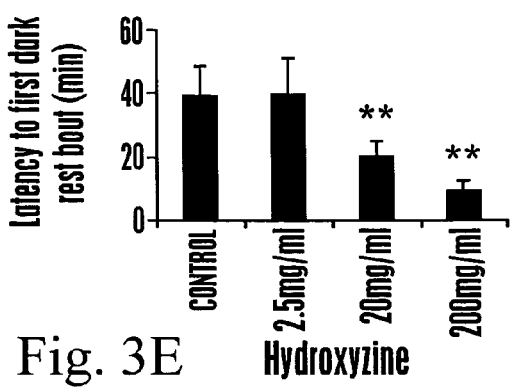
FIG. 3E shows latency to first dark rest, in *Drosophila* given the indicated doses of hydroxyzine beginning in the final hour of the light period.

Histamine has been shown to be a neurotransmitter in the central and peripheral nervous system of the fly (Nassel, *Microsc. Res. Tech.* 44:121 (1999)). When flies were given hydroxyzine, an antagonist of the Hl histamine receptor, rest during the first hour of the dark period was increased in a dose-dependent manner (FIG. 3D), and latency to first dark period rest was decreased (FIG. 3E) (n=4O/dose, *, $p=0.056$; **, $p<0.001$). The increase in rest was not associated with a general impairment of fly behavior. The activity per waking minute was unchanged during the dark period (both during the first hour and the subsequent hours). The total amount of activity during the light period was also unchanged. Furthermore, responsiveness to arousing stimuli was preserved.

Thus, two agents that modulate waking and sleep in mammals also modulate vigilance states in *Drosophila*.

EXAMPLE IV

Molecular Correlates of Sleep in *Drosophila*

This example shows that *Drosophila* gene expression is modulated by vigilance state, in a similar manner as it is in mammals.

Recently, several genes have been identified whose expression in the rat brain changes in relation to sleep and waking (see Cirelli et al., *Mol. Brain Res.* 56:293 (1998); Cirelli et al., *Ann. Med.* 31:117 (1999); Cirelli et al., *Sleep* 22(S):113 (1999)). In order to determine whether there are any molecular changes associated with the rest-activity cycle in the fly, gene expression in *Drosophila* was systematically screened using mRNA differential display as well as a targeted approach with RNase protection assays (RPA) to search for specific genes.

mRNA differential display and RPA were performed as in Cirelli et al., *Mol. Brain Res.* 56:293 (1998), with the following modifications. For differential display, reverse transcription was performed with 0.5 pg of pooled total RNA from fly heads (n=20). Two independent pools were reverse-transcribed per condition. PCR reactions were performed in duplicate for each pool. One hundred and four combinations of primers were used. For RPA, 1-2 µg of total RNA from pooled fly heads (n=60) were used. The amount of sample RNA was normalized using a riboprobe specific for ribosomal protein rp49.

RNA was extracted from whole heads of flies that (I) had been spontaneously resting for 3 h during the dark period; (ii) had been rest deprived for 3 h and were collected at the same circadian time, or (iii) had been spontaneously awake for 3 h during the light period (see FIG. 4A). This allowed distinguishing between changes in gene expression associated with behavioral state and those associated with circadian time or with stimulation.

The behavioral state was determined individually for each fly; only flies that satisfied specific criteria were selected for analysis. In particular, a fly was considered to be awake if it was active for at least 90% of the 3-hour light period and 100% of the hour before sacrifice. A fly was resting if it was inactive for at least 66% of the 3-hour dark period and 100% of the hour before sacrifice. Only about 60-70% of the flies examined satisfied these criteria. It should be noted that failure to specifically identify rest and waking, as has been done in circadian screens, results in samples containing a mixture of behavioral states.

Similar to what has been shown in rat, it was determined that about 1% of the transcripts examined in *Drosophila* were modulated by behavioral state. Out of an estimated 5,000 RNA species screened, 54 were expressed at higher levels during waking than during rest and 28 were higher during rest.

Several transcripts (46) showed a prominent circadian, but not state-dependent, modulation (Van Gelder et al., *Curr. Biol.* 5: 1424 (1995)). For example, a transcript designated "Circadian" was increased by 400% in the dark conditions (both rest and rest deprivation) with respect to the light condition (waking). This transcript did not correspond to any known sequence. An additional gene which showed a circadian, but not state-dependent, modulation was *Drosophila* fos (Perkins et al., *Genes Dev.* 4:822 (1990)). D-fos was expressed at higher levels during the dark hours, irrespective of behavioral state. By contrast, in rat (and cat) c-fos is high during waking and low during sleep, irrespective of circadian time (Pompeiano et al., *J. Sleep Res.* 3:80 (1994)). In the rat suprachiasmatic nucleus, c-fos expression is modulated in a circadian way by light (Schwartz et al., *Sem. Neurosci.* 7:53 (1995)). It should be noted that the transcriptional activity of CREB, which is necessary for fos induction, is also higher during the dark hours in *Drosophila* (Belvin et al., *Neuron* 22:777 (1999)).

An example of a transcript whose expression was higher after periods of rest was designated "Rest". As confirmed using RPA, this mRNA was 45% higher in rest than in rest deprivation. None of the rest-related transcripts matched any published sequence, similar to the results in the rat.

By contrast, several known genes were identified that were expressed at higher levels during waking than during rest, irrespective of circadian time (p<0.1, ANOVA). One, with high homology to Fatty acid synthase (Fas), was increased after 3 h of spontaneous waking or rest deprivation compared to rest (by 50% and 88%, respectively, using RPA, as shown in FIG. 4B, top). This sequence matched a *Drosophila* Pl Clone (AC005554). Subsequent analysis using Genescan indicated that the sequence matched a proposed peptide that had 49% homology with rat FAS.

Since Fas expression had not been studied in the fly, in situ hybridization with digoxigenin-labeled probes was performed as described in Aronstein et al., *Neuroscience* 2:115 (1996). In situ analyis indicated that the Fas transcript is expressed throughout the fly brain, including the optic lobes, but not in the eye. Although the role of this enzyme in the fly brain not clear, fatty acids are increasingly being recognized as modulators of neural activity (see Clark, *Evolution* 44:637 (1990); Yehuda et al., *Peptides* 19:407 (1998)).

Significantly, several genes were identified that were upregulated during waking. vs. rest in the fly that corresponded to genes upregulated during waking vs. sleep in the rat, irrespective of circadian time. In the rat, mitochondrial genes, including Cytochrome oxidase C, subunit I, show a rapid increase in expression during the first few hours of waking (Cirelli et al., *Mol. Brain Res.* 56, 293 (1998); Cirelli et al., *Ann. Med.* 31:117 (1999); Cirelli et al., *Sleep* 22(S):113 (1999) and FIG. 4C, bottom). In *Drosophila*, mRNA levels of Cytochrome oxidase C, subunit I, also show a rapid increase during the first few hours of waking with respect to rest (FIG. 4C, top). Such rapid changes in the expression of the mitochondrial genome are thought to represent a local response of nervous tissue to the increased metabolic requirements of waking (Wong-Riley et al., *Neuroscience* 76, 1035 (1997); Cirelli et al., *Mol. Brain Res.* 56:293 (1998)).

Cytochrome P450 (Cyp4e2), a member of a large family of detoxifying enzymes (Dunkov et al., *Mol. Gen. Genet.* 251: 290 (1996)), was also increased in waking and rest deprivation with respect to rest by 77% and 99%, respectively (FIG. 4B, bottom). A related cytochrome P450 (Cyp4F5) was upregulated after periods of waking in rat cerebral cortex, as demonstrated by using gene discovery arrays and RPA (Rat Atlas cDNA 1.2 expression array (Clontech)).

BiP is a chaperone protein localized in the endoplasmic reticulum that assists in the folding and assembly of newly synthesized secretory and transmembrane proteins. BiP may also serve as a calcium buffer (Pahl et al., *Physiol. Rev.* 79:683 (1999)). In *Aplysia*, the homologue of BiP is upregulated within 3 h of behavioral training and is thought to promote the structural changes necessary for the establishment of long-term memory (Kuhl et al., *J. Cell Biol.* 119:1069 (1992)). FIG. 4D (bottom) shows that, in the rat, BiP mRNA is expressed at higher levels after periods of spontaneous waking and sleep deprivation (8 h) than after periods of sleep. A similar pattern is found in *Drosophila* (FIG. 4D, top). After spontaneous waking and rest deprivation (3 h), BiP mRNA exhibits a 2-fold and 3-fold increase above resting values, respectively.

It was also determined that mRNA levels of arylalkyamine N-acetyl transferase (Dat) were increased by 48% after 2-3 h of waking compared to rest. This enzyme, which is found in *Drosophila* brain, is involved in the catabolism of monoamines such as tryptamine, tyramine, serotonin, dopamine, and octopamine (Hintermann et al., *Proc. Natl. Acad. Sci. USA* 93:12315 (1996); Brodbeck et al., *DNA Cell Biol.* 17:621 (1998)). In rats, waking is associated with a marked increase in brain mRNA for arylsulfotransferase, another enzyme implicated in the catabolism of monoamines (Cirelli et al., *Mol. Brain Res.* 56, 293 (1998); Cirelli et al., *Ann. Med.* 31:117 (1999); Cirelli et al., *Sleep* 22(S):113 (1999)). These findings are of importance because, in the species tested so far, waking is associated with high central monoaminergic activity, while a reduction of such activity is a hallmark of sleep (McGinty et al., *Brain Res.* 101: 569 (1976); Aston-Jones et al., 1:876 (1981)). This has led to the suggestion that sleep may serve to counteract the effects of continued monoaminergic discharge. According to this hypothesis, an impaired catabolism of monoamines should result in an increased need for sleep (Hartmann et al., *Functions of Sleep*, (Yale University Press, New Haven (1973); Siegel et al., *Brain Res. Rev.* 13:213 (1988); Jouvet, *Neuropsychopharm.* 21, 24S (1999)).

Figure 5A:
FIG. 5A shows the number of infrared beam crossings per day in wild-type, $Dat^{lo}/Dat^{lo}$ and $Dat^{lo}/Df$ flies ($p>0.05$, $n=25$).
Figure 5B:
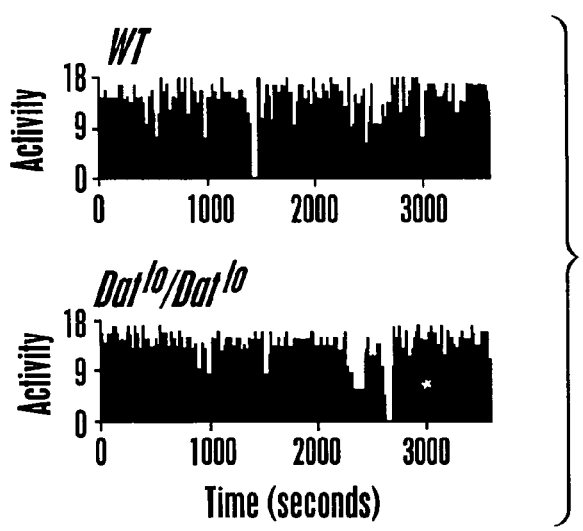
FIG. 5B shows activity patterns as measured by the ultrasound system in wild-type, $Dat^{lo}/Dat^{lo}$ and $Dat^{lo}/Df$ flies (representative activity records for 1 h during the light period are shown).
Figure 5C:
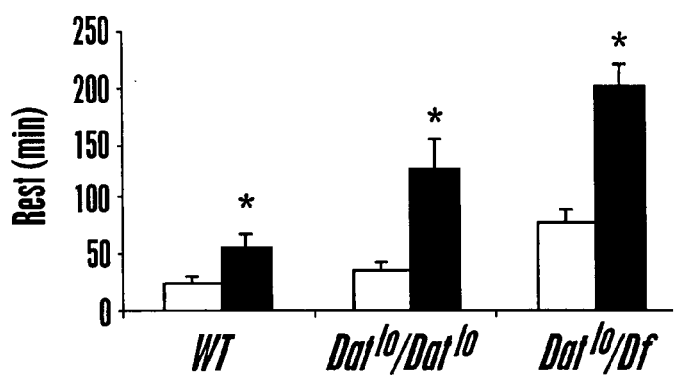
FIG. 5C rest rebound in wild-type, $Dat^{lo}/Dat^{lo}$ and $Dat^{lo}/Df$ flies during the first 6 h of recovery.

To evaluate this possibility, a *Drosophila* mutant was used in which the activity of the Dat enzyme is deficient ($Dat^{lo}$). $Dat^{lo}$ is a hypomorphic allele of AANAT1b. Insertion of blastopia into the first intron results in 10% of wildtype dopamine acetyltransferase activity. As indicated by both the infrared and ultrasound monitoring systems, flies homozygous for the $Dat^{lo}$ mutation did not differ from wild-types in the percentage and circadian distribution of rest and waking under baseline conditions (FIG. 5A). They also showed normal amounts and patterns of activity (FIG. 5B). Each strain obtained >90% of their daily rest during the dark period. However, following 12 h of rest deprivation during the dark period, it was found that Dat$^{lo}$ flies displayed a rest rebound that was much greater than in rest deprived controls (189%) (FIG. 5C).

Figure 5D:
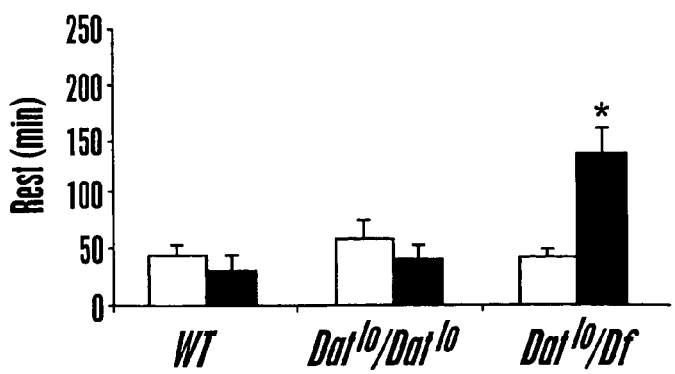
FIG. 5D shows rest rebound in wild-type $Dat^{lo}/Dat^{lo}$ and $Dat^{lo}/Df$ flies during the second 6 h of recovery.

To confirm that this phenotype maps to the Dat locus and to assay for gene dosage effects, flies with one dose of the Dat$^{lo}$ mutation (hemizygous) were generated by crossing Dat$^{lo}$ homozygotes with flies carrying a deficiency (Df) of the Dat locus, Df(2R)Px1. Flies hemizygous for the Dat$^{lo}$ mutation (Dat$^{lo}$/Df) did not differ from wild-types or Dat$^{lo}$ homozygotes in the percentage and circadian distribution of rest and waking under baseline conditions (FIG. 5A). Dat$^{lo}$/Df flies showed not only an increased rest rebound during the first 6 h of recovery compared to wild-type flies (FIG. 5C), but also a persistent rebound during the second 6 h of recovery (FIG. 5D). These results indicate that the more severely mutant the fly is at the Dat locus, the greater the rebound. Although the mechanism responsible for the increased homeostatic response to rest deprivation is not clear, these results suggest a linkage between the catabolism of monoamines and the regulation of sleep and waking in *Drosophila*.

In order to evaluate whether other genes involved in monoamine catabolism are associated with altered vigilance, mutants in Dopa decarboxylase (Ddc) were evaluated. Dopa decaryboxylase (Ddc) is involved in the final step in the synthesis of the neurotransmitter dopamine. Two genotypes, Ddc[ts2]/+ and Ddc[27]/+, both heterozygous for Ddc mutations, were tested. Ddc[ts2]/+ has somewhat more enzyme activity than Ddc[27]/+. Ddc[ts2]/+ and Ddc[27]/+ *Drosophila* were tested initially for activity and sleep, both of which were normal. Ddc[ts2]/+ and Ddc[27]/+ *Drosophila* were then tested for rebound effect after sleep deprivation. Both Ddc[ts2]/+ and Ddc[27]/+ *Drosophila* exhibited approximately half as much rebound as wild-type flies. Moreover, the rebound in Ddc[27]/+ flies (2 hr long) was shorter than in Ddc[ts2]/+ flies (4 hr long), as compared to wild-type (6 hr long). These results are consistent with a role for Ddc in homeostatic regulation of sleep. More specifically, the less Ddc enzyme activity, the less rebound.

The results observed with Ddc mutants are also consistent with the Dat results. Dat mutants fail to degrade several neurotransmitters, including dopamine. The less Dat activity the flies have, the more and longer rebound they show. The Ddc mutants exhibit opposite behavior—the less neurotransmitter produced, the less rebound. Thus, there is an apparent correlation between the accumulation of neurotransmitters such as dopamine and the amount of rebound.

Taken together, the results shown in Examples I-IV indicate that rest in invertebrates is very similar to mammalian sleep, as evidenced by increased arousal threshold, homeostatic regulation, dependence on age, sensitivity to pharmacological manipulation, and expression of similar vigilance-modulated genes.

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention. Accordingly, the invention is limited only by the claims.

We claim:

1. A method of identifying a vigilance enhancing compound that modulates homeostatic regulation, comprising:
    (a) contacting an invertebrate with a candidate vigilance enhancing compound,
    (b) determining the effect of said candidate compound on a homeostatic regulatory property of vigilance selected from the group consisting of sleep rebound, wake period, latency to sleep, rate of sleep wake transition, alertness and drowsiness by comparing said effect to a baseline or established value for the property in an untreated control, wherein a compound that alters said homeostatic regulatory property is characterized as being a vigilance enhancing compound that modulates homeostatic regulation.

2. A method of identifying a vigilance diminishing compound that modulates homeostatic regulation, comprising:
    (a) contacting an invertebrate with a candidate vigilance diminishing compound,
    (b) determining the effect of said candidate compound on a homeostatic regulatory property of vigilance selected from the group consisting of sleep rebound, wake period, latency to sleep, rate of sleep wake transition, alertness and drowsiness by comparing said effect to a baseline or established value for the property in an untreated control, wherein a compound that alters said homeostatic regulatory property is characterized as being a vigilance diminishing compound that modulates homeostatic regulation.

* * * * *